US012662659B2

(12) United States Patent
  Gorio

(10) Patent No.: US 12,662,659 B2
(45) Date of Patent: *Jun. 23, 2026

(54) METHOD FOR PROMOTING AND IMPROVING PROPERTIES OF ADIPOSE TISSUE , TISSUE AND CELLS OBTAINED BY SAID METHOD

(71) Applicant: Surgere S.r.I., Trento (IT)

(72) Inventor: Alfredo Gorio, Milan (IT)

( * ) Notice: Subject to any disclaimer, the term of this patent is extended or adjusted under 35 U.S.C. 154(b) by 573 days.

This patent is subject to a terminal disclaimer.

(21) Appl. No.: 16/066,976

(22) PCT Filed: Dec. 28, 2016

(86) PCT No.: PCT/IB2016/058035
  § 371 (c)(1),
  (2) Date: Jun. 28, 2018

(87) PCT Pub. No.: WO2017/115289
  PCT Pub. Date: Jul. 6, 2017

(65) Prior Publication Data
  US 2019/0024055 A1    Jan. 24, 2019

(30) Foreign Application Priority Data
  Dec. 30, 2015   (IT) ......................... 102015000089292

(51) Int. Cl.
  *C12N 5/0775* (2010.01)
  *A61K 35/28* (2015.01)

(52) U.S. Cl.
  CPC ............ *C12N 5/0667* (2013.01); *A61K 35/28* (2013.01); *C12N 2527/00* (2013.01)

(58) Field of Classification Search
  CPC .............................. B01F 25/10; C12N 5/0667
  See application file for complete search history.

(56) References Cited

U.S. PATENT DOCUMENTS

| 2008/0044899 A1* | 2/2008 | Kano ................... | C12N 5/0667 |
| | | | 435/368 |
| 2011/0086426 A1* | 4/2011 | Freund ................... | C12M 45/05 |
| | | | 435/379 |
| 2011/0311984 A1 | 12/2011 | Paek | |
| 2013/0034524 A1 | 2/2013 | Agha-Mohammadi | |
| 2014/0024011 A1* | 1/2014 | Harris ................... | A01N 1/0284 |
| | | | 435/1.3 |

FOREIGN PATENT DOCUMENTS

| WO | WO-2011134957 A1 * | 11/2011 | ........... A61F 2/0077 |
| WO | 2014178438 | 5/2014 | |
| WO | 2015174871 | 5/2015 | |

OTHER PUBLICATIONS

Carelli et al, "Characteristics and Properties of Mesenchymal Stem Cells Derived From Microfragmented Adipose Tissue", Cell Transplantation, published May 2014, vol. 24, pp. 1233-1252. (Year: 2014).*

Carelli et al., "Mechanical Activation of Adipose Tissue and Derived Mesenchymal Stem Cells: Novel Anti-Inflammatory Properties", International Journal of Molecular Sciences, 2018, 19(1), 267, pp. 1-16 (Year: 2018).*

S. D. Dave et al: "Extrinsic Factors Promoting In Vitro Differentiation of Insulin-Secreting Cells from Human Adipose Tissue-Derived Mesenchymal Stem Cells", Applied Biochemistry and Biotechnology, vol. 170, No. 4, Jun. 1, 2013 (Jun. 1, 2013), pp. 962-971, XP055284868, United States ISSN: 0273-2289, DOI: 10.1007/s12010-013-0250-y p. 964, paragraph 3.

Bradley T Estes et al: "Isolation of adipose-derived stem cells and their induction to a chondrogenic phenotype", Nature Protocols, vol. 5, No. 7, Jul. 1, 2010 (Jul. 1, 2010), pp. 1294-1311, XP055283960, GB ISSN: 1754-2189, DOI: 10.1038/nprot.2010.81 See step 8 of the protocol on p. 1300.

Schwerk Anne et al: "Adipose-derived human mesenchymal stem cells induce long-term neurogenic and anti-inflammatory effects and improve cognitive but not motor performance in a rat model of Parkinson's disease", Regenerative Medicineenglandmay 2015,, vol. 10, No. 4, May 1, 2015 (May 1, 2015), pp. 431-446, XP009190726, ISSN: 1746-076X The whole document.

Berg Jurgen et al: "Human adipose-Derived Mesenchymal Stem Cells Improve Motor Functions and are Neuroprotective in the 6-Hydroxydopamine-Rat Model for Parkinson's Disease when Cultured in Monolayer Cultures but Suppress Hippocampal Neurogenesis and Hippocampal Memory Function when Cultured in Spher", Stem Cell Reviews, Humana Press Inc, US, vol. 11, No. 1, Aug. 15, 2014 (Aug. 15, 2014), pp. 133-149, XP035452945, ISSN: 1550-8943, DOI: 10.1007/S12015-014-9551-Y.

Choi Hee Soon et al: "Therapeutic potentials of human adipose-derived stem cells on the mouse model of Parkinson's disease", Neurobiology of Aging, vol. 36, No. 10, Jun. 24, 2015 (Jun. 24, 2015) , pp. 2885-2892, XP029264313, ISSN: 0197-4580, DOI: 10.1016/J.NEUROBIOLAGING.2015.06.022 The whole document.

M. Boschert et al., "Analysis of lipocyte viability after liposuction," Plast. Reconstr. Surg., Feb. 2002; 109(2):761-5.

Alireza Tavakolinejad, Mohsen Rabbani, Mohsen Janmaleki, Effects of hypergravity on adipose-derived stem cell morphology, mechanical property and proliferation, Biochemical and Biophysical Research Communications, vol. 464, Issue 2, 2015, pp. 473-479, ISSN 0006-291X, https://doi.org/10.1016/j.bbrc.2015.06.160.

Takayuki Nakayama, Hidefumi Kato, Cell Therapy Using Adipose-Derived Mesenchymal Stromal Cells: Current Status and Perspectives, Japanese Journal of Transfusion and Cell Therapy, 2013, vol. 59, Issue 3, pp. 450-456, Released Jul. 19, 2013, Online ISSN 1883-0625, Print ISSN 1881-3011, https://doi.org/10.3925/jtc.59.450, https://www.jstage.jst.go.jp/article/jtc/59/3/59_450/_article/-char/en, Abstract: [in Japanese].

Japanese Patent Office, Examination Report, Jun. 22, 2021.

* cited by examiner

*Primary Examiner* — Laura Schuberg

(74) *Attorney, Agent, or Firm* — Themis Law

(57) ABSTRACT

A method for promoting anti-inflammatory properties and for improving repair ability of a tissue containing mesenchymal stem cells (MSCs) includes causing a mechanical activation by applying a orbital shaking force on an adipose tissue lipoaspirated or removed from a body.

7 Claims, 30 Drawing Sheets

Pz 59 (p 9)

Pz 59 (p2)

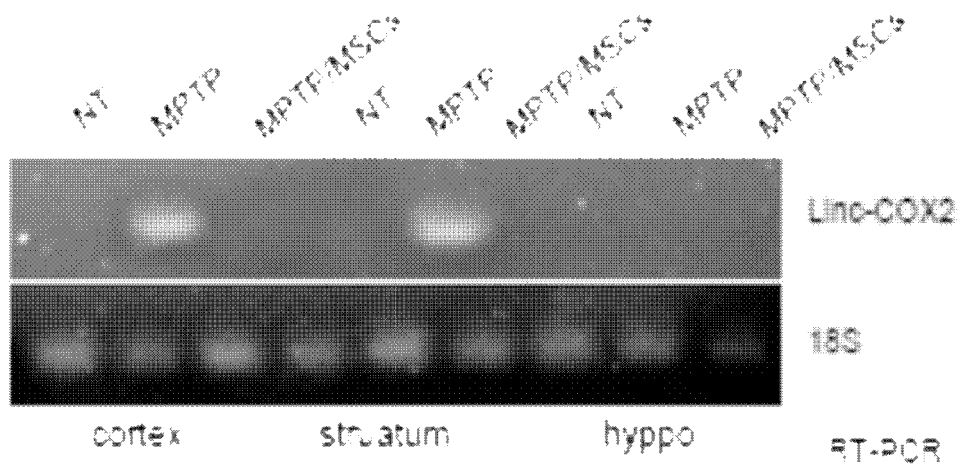
Fig.16A
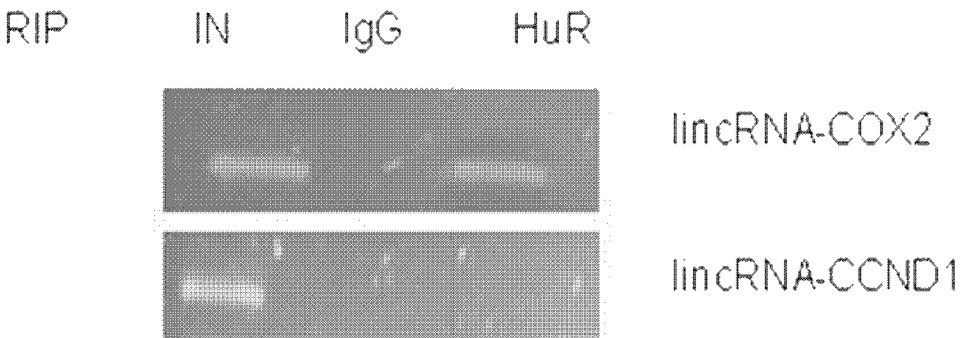
Fig.16B
ERROR IN FORELIMB                    VERTICAL GRID
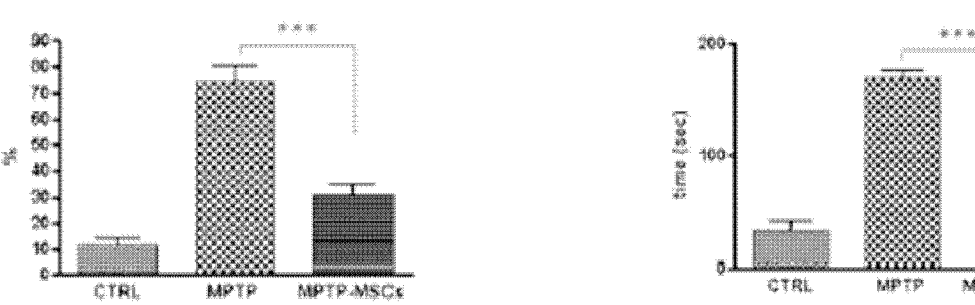
Fig.16C
Fig.16D

CYTOKINE EXPRESSION (48 HOURS)

* p < 0.05;  p<0.01; * p<0.001 vs LES

Fig. 24 a    NESTIN    Contusion 70Kdyne    Fig. 24 b

CTRL

Contusion 70Kdyne + LS

Contusion 70Kdyne + MALS

Contusion 70Kdyne + MALS.

Nestin

MALS at 4 weeks

Contusion 70Kdyne + MALS. Nestin
Neurogenesis in SCI

1

METHOD FOR PROMOTING AND IMPROVING PROPERTIES OF ADIPOSE TISSUE , TISSUE AND CELLS OBTAINED BY SAID METHOD

The present invention relates to a method for promoting anti-inflammatory properties and for improving repair ability of a tissue containing mesenchymal stem cells (MSCs), to the tissue and to mesenchymal stem cells obtained by said method.

It is known to prepare tissues that can repair, replace or restore structures and/or impaired biological functions resulting from congenital defects, ageing, diseases, or destruction thereof (Haseltine, 2003; Gutmann et al., 2005, Greenwood. et al., 2006).

Mesenchymal stem cells (MSCs) are multi-potent cells, able to self-renew and able to differentiate, in vitro, into cells of mesenchymal origin, including osteoblasts, adipocytes and chondrocytes, and able to give rise to tissues such as bone, fat, cartilage and muscle, in vivo (Pittenger et al., 1999). Recent studies have proved that the capacity of tissue regeneration can be improved by using mesenchymal stem cells derived from human adipose tissue (so called hADSCs) (Gimble et al., 2011).

The number of mesenchymal stem cells seems to be considerably higher in adipose tissue than in other tissues, such as bone marrow (Bieback et al., 2004).

The autologous transplantation of adipose tissue is a well-known therapeutic procedure, used for repairing several damages to tissues.

Moreover several recent publications disclose that human adipose-derived stem cells (hADSCs) are able, being properly stimulated, to differentiate in other different types of cells, such as neurons, cardiomyocytes, hepatocytes, and pancreatic cells (Schaffler et al., 2007; Strem et al., 2005) and have a clinical potential for vasculogenesis (Madonna et al., 2009), osteogenesis (Shenaq et al., 2010) and neuronal repair models (Wakabayashi et al., 2010).

It is also known that mechanical forces can be very important for adult tissue plasticity, as it occurs during embryogenesis, tissue remodeling and mitotic and motility behavior of cells (Vogel et al., 2006).

Cells perceive and respond to forces applied from the outside and to forces exerted on the cell matrix and on cell-cell contacts.

Ion channels activated by stretch, growth factors, cyto-skeletal strands, extracellular matrixes, focal adhesions, and tyrosine kinase are involved in the conversion of mechanical stimuli into biochemical signals in cells (mechanotransduction) that lead to downstream events and therefore guide key messages on fate to the nucleus (El Haj et al., 1999, Na et al., 2008; Walker et al., 2000, Venkatesan Iyer et al., 2012, Chen et al., 2013).

An important challenge in regenerative medicine is the minimal manipulation of stem cells, such to easily transform a specific cell line in cell therapy.

"Minimal manipulation" means a processing that does not alter the original relevant characteristics of the tissue relating to the tissue's utility for reconstruction, repair, or replacement (www.ema.europe.eu; www.fda.gov).

Regulatory agencies (FDA and EMA) and the International Society for Stem Cell Research (ISSCR) state that cell therapy should be considered as a medicine when there is more than one "minimal manipulation" of cells intended for clinical application or when the intended use of the cells is different from their usual function in the body (www.ema.europe.eu; www.fda.gov; Hyun et al., 2008).

Regulatory agencies state that patient protection is the core of such rules. In addition to the application of the same safety and efficacy rules, as for all the medicines, the quality and production of cell-based products declared in the requirements of good-manufacturing practice (GMP). These are standards recognized overall for guaranteeing the quality in producing and controlling medicines. Any use of such cell-based medicines is subjected to authorization and controls, including the procedure for manufacturing them (www.ema.europe.eu; www.fda.gov). According to regulatory agencies, in the cell culture in vitro, it is necessary to consider said rules to guarantee the growth and manipulation of isolated cells as acceptable. The processing steps shall be properly designed to preserve integrity and to control the function of the cells. Any manipulation procedures shall be documented in details and closely monitored according to specific process controls. The duration of cell culture and maximum number of cell passages shall be clearly specified and validated. The relevant genotypic and phenotypic characteristics of primary cell cultures, of established cell lines and the derived cell clones shall be defined and their stability, with respect to culture longevity, determined. Consistency and repeatability of the cell culture process shall be demonstrated and the culture conditions, including the media and the duration shall be optimized with respect to the intended clinical function of the cells. For such reasons, research on stem cells applied to regenerative medicine has to adhere to the main concept of "minimal manipulation".

It is also known that as people get older, the handling of Parkinson's disease is a more and more important and demanding aspect of medical practice for neurologists and general practice doctors.

Parkinson's disease (PD) is a common neurodegenerative disease, a synucleinopathy, with a prevalence of 160/100 000 units in Western Europe, till involving about 4% of the population over 80 years old.

The comprehension of the pathogenesis of the disease has improved in the last ten years and for example important progresses have been made in creating cells producing dopamine from stem cells.

The general object of the present invention is to activate at molecular and cellular level the adipose tissue, for example removed by liposuction, in a very simple, cheap and particularly functional manner.

A further object of the present invention is to have a minimal manipulation of cells, particularly of mesenchymal stem cells, derived from adipose tissue, without chemical digestion of said tissue.

Another object is to change the inflammatory condition of a adipose tissue, particularly to trigger anti-inflammatory properties and to suppress the production of inflammatory cytokines such as TNF-alpha (tumor necrosis factor-alpha) in human adipose tissue obtained for example by liposuction, and to improve the tissue repair ability, by a minimal manipulation procedure, such to use mesenchymal stem cells obtained from human adipose tissue (called as hADSCs) for therapeutic purposes.

Considering the above objects, according to the present invention, we have thought of providing a method for promoting anti-inflammatory properties and for improving the repair capacity of a tissue containing mesenchymal stem cells (MSCs), a adipose tissue obtained by said method and mesenchymal stem cells derived from said tissue, having the characteristics disclosed in the annexed main claims and in the subclaims.

According to the present invention the method comprises at least one mechanical activation step performed by applying an orbital shaking force on a adipose tissue lipoaspirated or removed from the body.

According to the present invention the force applied on the adipose tissue lipoaspirated or removed from the body has an intensity ranging from 40 to 120×g.

In a preferred embodiment such applied force has intensity equal to 97×g.

Said force is applied for a time ranging from 3 to 20 minutes.

For example said force is applied for 10 minutes.

It is possible to provide to apply the force to the adipose tissue lipoaspirated or anyway removed from the human or animal body by any known technique, and contained in a suitable container, only once or it is possible to provide said force to be applied two or more times in a manner repeated over time.

For each repetition, the force intensity as well as the duration of each application can be the same or different.

The method of the present invention can be applied both to fresh adipose tissue and to cryopreserved tissue.

The orbital shaking force can be applied to the adipose tissue lipoaspirated or removed from the body by a device composed of a motor with an orbital movement provided with a disposable and sterile container, inside which the adipose tissue lipoaspirated or removed from the body is contained, which has a capacity up to 500 ml.

The present invention relates also to a tissue obtained by said method and stem cells obtained from said tissue by a further step of isolating and expanding said mesenchymal stem cells contained in said adipose tissue lipoaspirated or removed from the body (hADSCs).

Particularly the adipose tissue and the mesenchymal stem cells obtained by the method of the present invention have improved anti-inflammatory properties and improved repair capacity, since in said tissue and mesenchymal stem cells:

the expression of inflammatory cytokines is eliminated such as tumor necrosis factor-alpha (TNF-alpha);

the expression of its natural inhibitor TSG-6 and of interleukin 15 is considerably enhanced;

the expression of leptin is considerably improved;

and the parameters that define the stemness are increased such as the expression of pluripotency-related genes (SOX2, OCT4, Nanog), of beta-tubulin III and TSG6 mRNA.

The mechanically activated adipose tissue, that is removed, preserved in a container and subjected to orbital shaking, is completely similar, from a structural point of view, to the tissue obtained by biopsy.

The object of the present invention is also the use of said tissue and mesenchymal stem cells in cell therapy.

Particularly and not as a limitation, stem cells present in the adipose tissue, for example said mesenchymal stem cells activated according to one or more of the characteristics and of the embodiments described above, are used in activation of endogenous stem cells of spinal cord.

Characteristics of the present invention and its advantages will be more clear and evident from an examination of the following description, referred to annexed figures showing experimental results.

In the figures:

FIGS. 1A, 1B and 1C are the differential expression of cytokines in lipoaspirated adipose tissue and in lipoaspirated adipose tissue after mechanical activation according to the present invention: TSG6 is already observable after 3 minutes of stimulation and it has maximum expression within 6-10 minutes; TNF-alpha is suppressed in 6 minutes. FIG. 1D shows that such effects are observable also in the cryopreserved adipose tissue; TQ=time 0, PZA=patient A, PZB=patient B, TNF-α=tumor necrosis factor-alpha, LEPT=leptin, IL15=interleukin 15;

FIG. 2 is the expression of pluripotency genes (SOX2, OCT4, Nanog), beta-tubulin III and TSG6 tested with real-time RT PCR in samples from biopsy of human adipose tissue, lipoaspirated and lipoaspirated mechanically activated by the method of the present invention (10 minutes). All the investigated genes are hardly activated in the regular bioptic tissue, that is non processed tissue, according to the present invention (biopsy), and are slightly activated by performing the known Coleman procedure after liposuction (lipoaspirate). Differently the upregulation is incomparably higher after the specific activation according to the present invention for 10 minutes;

Figure 8B:
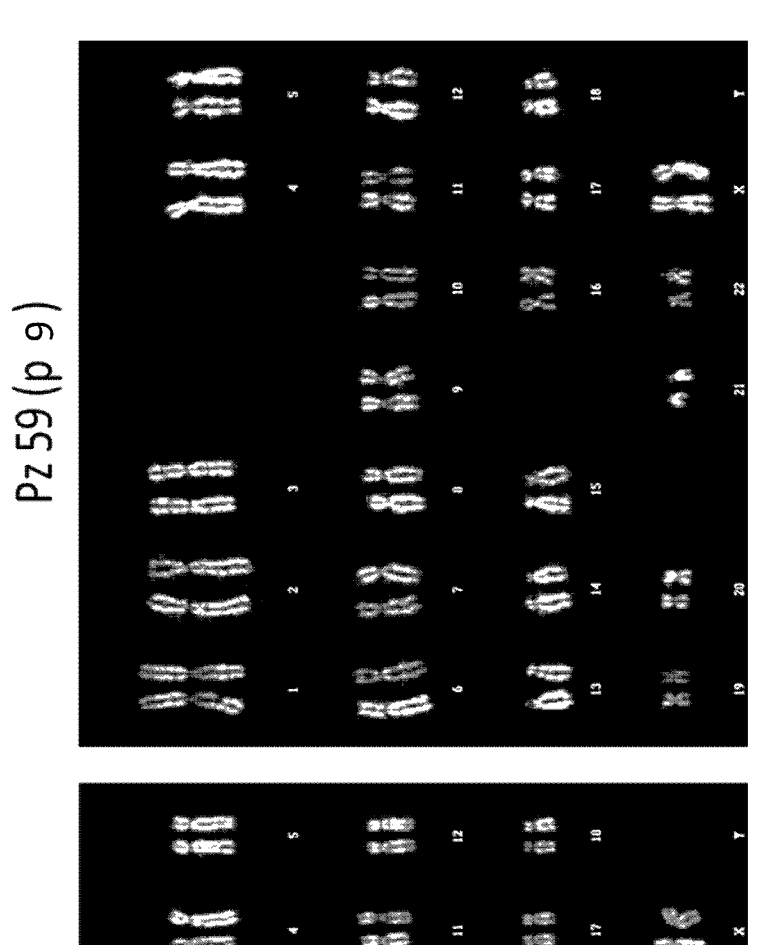
Figure 8A:
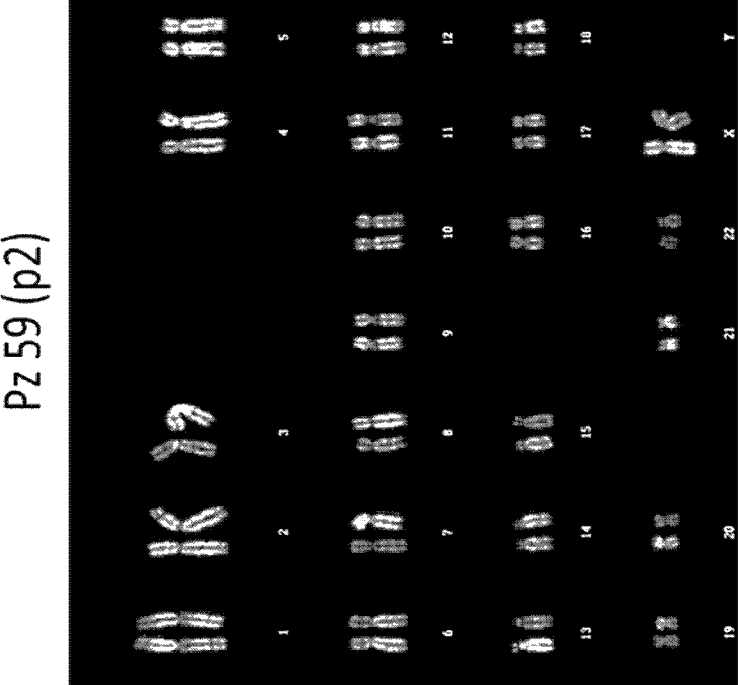
Figure 9:
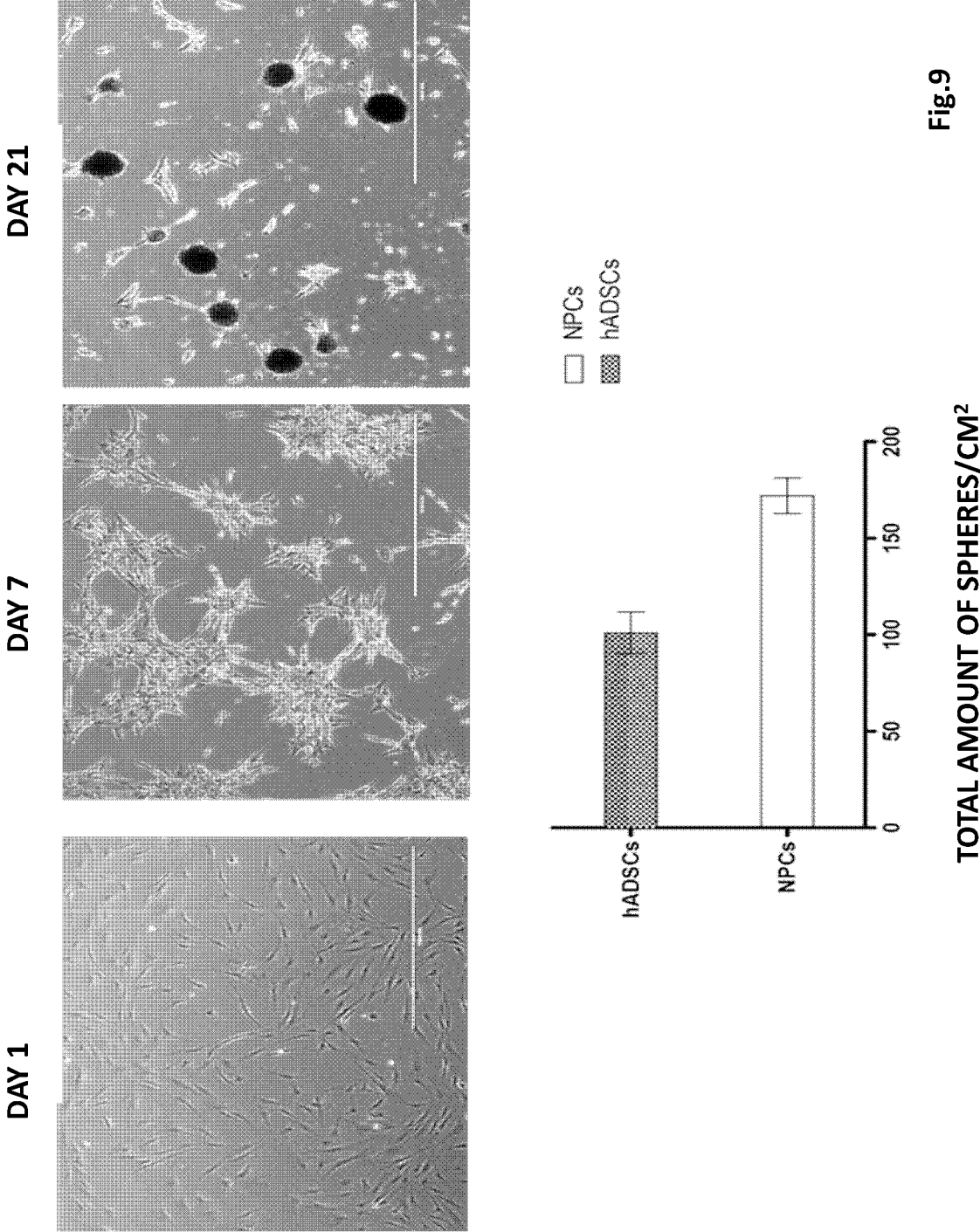
Figure 10:
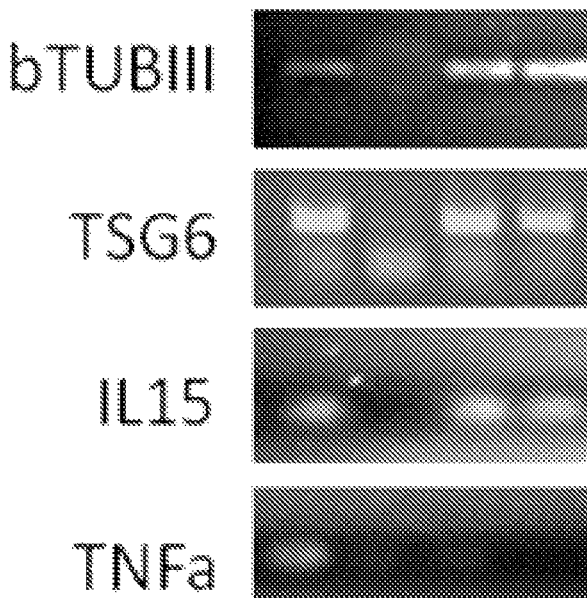
Figure 11:
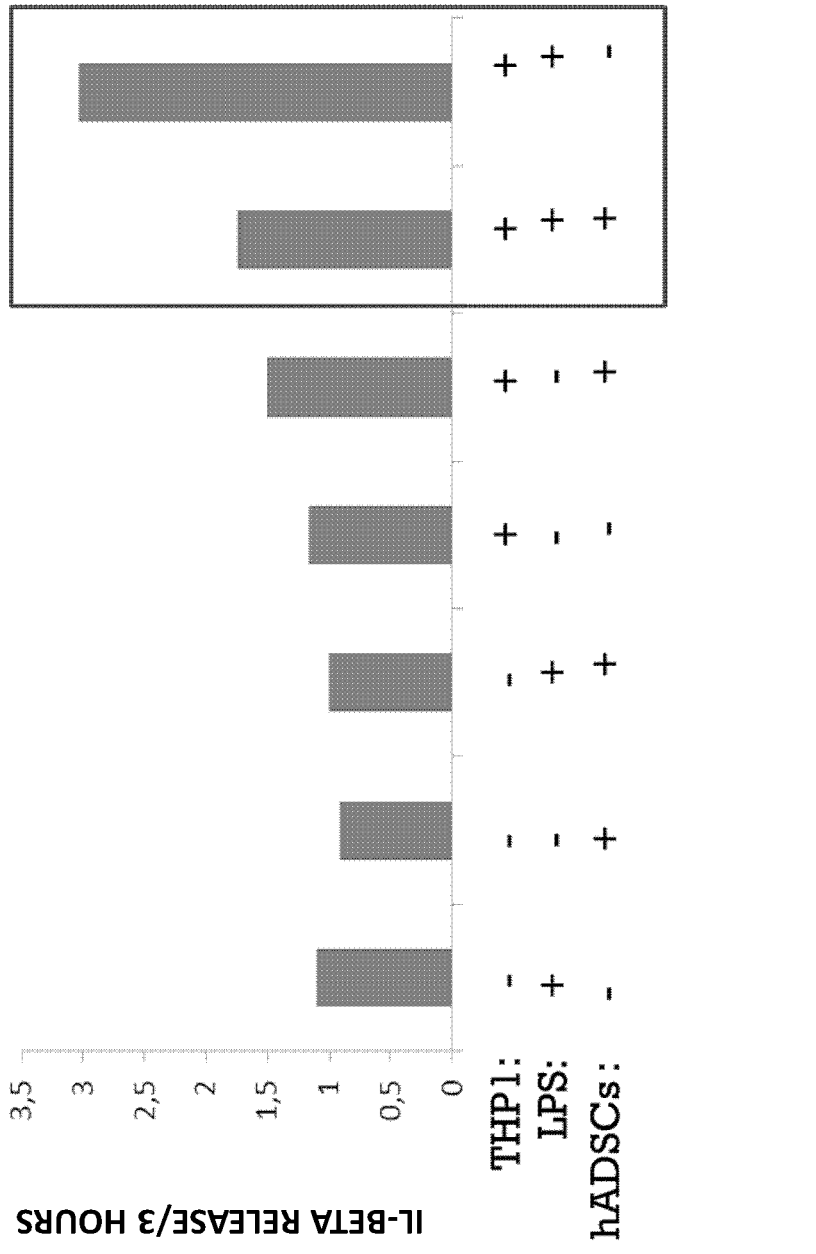
Figure 12:
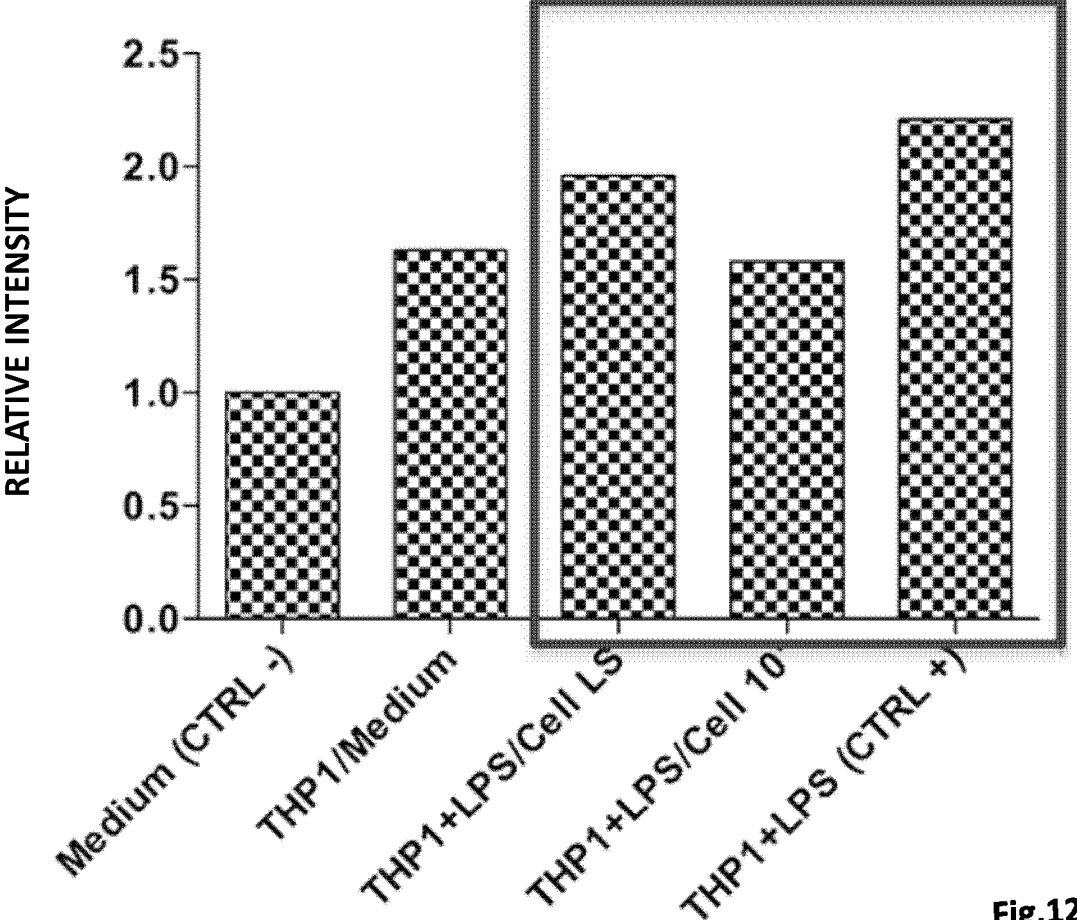
Figure 13:
Figure 13:
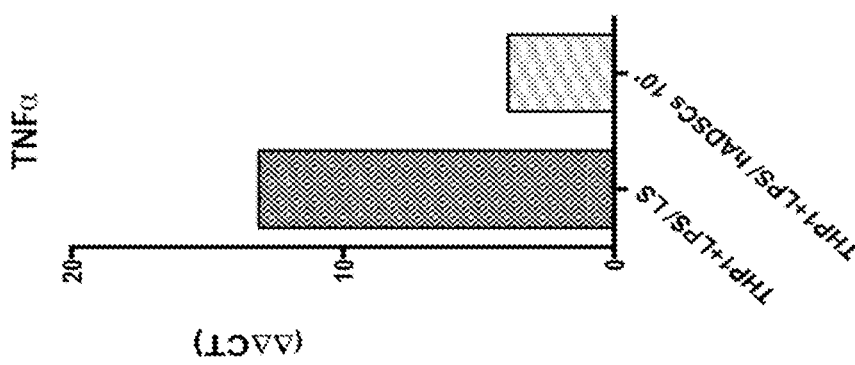
Figure 13:
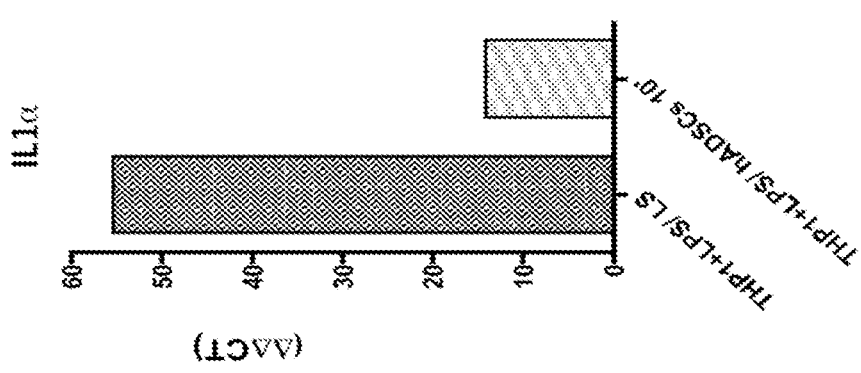
Figure 14:
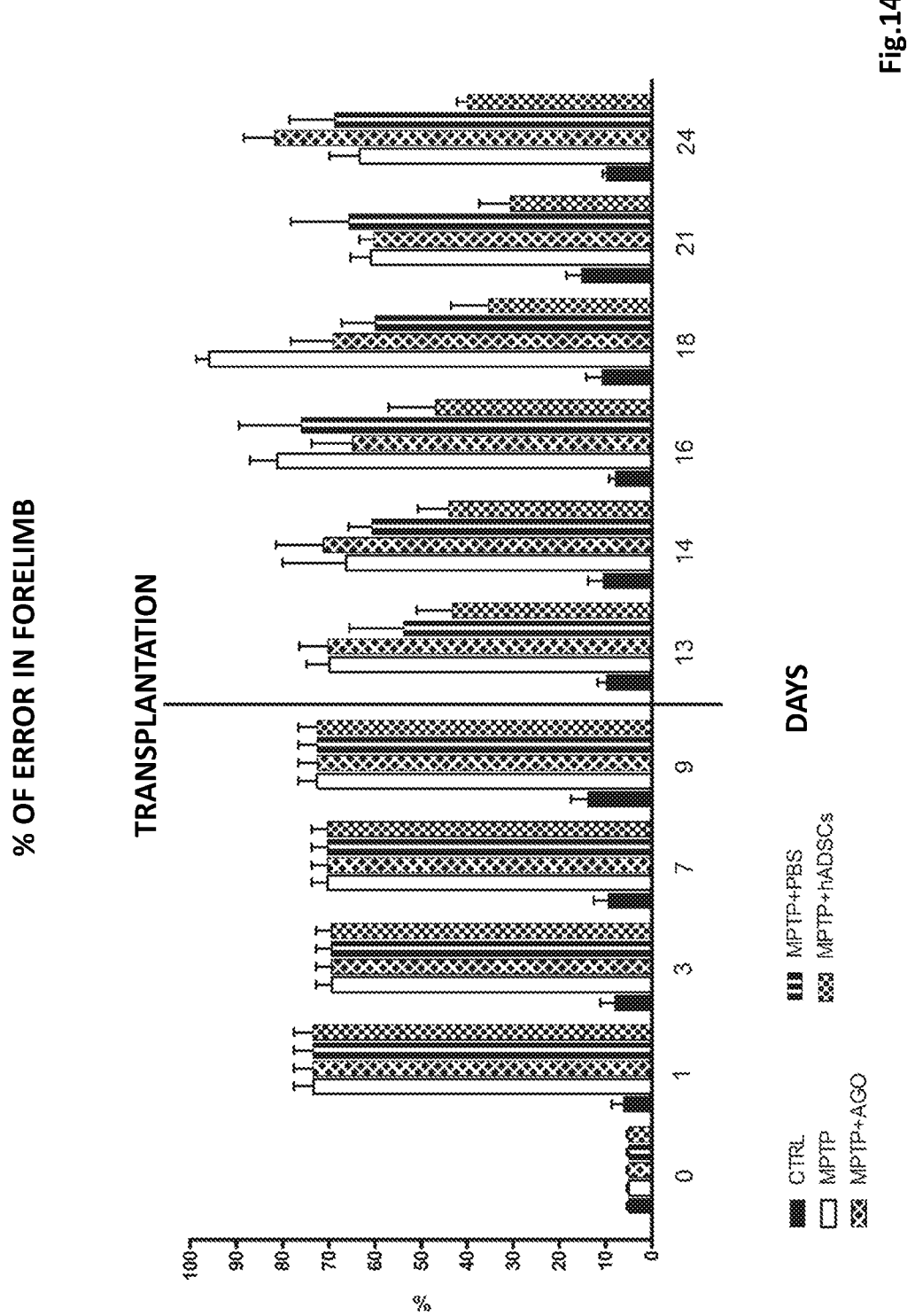
Figure 15:
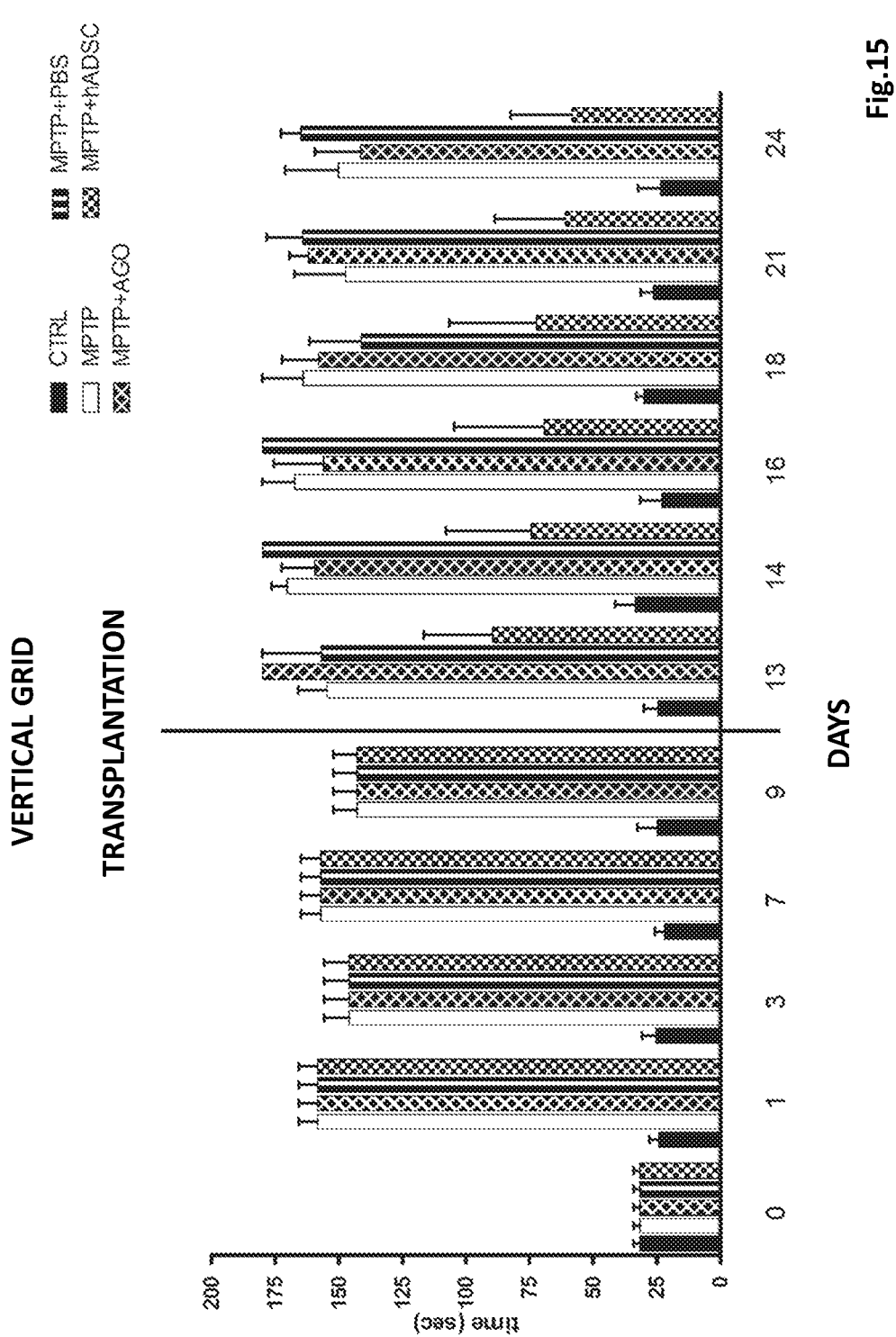
Figure 17:
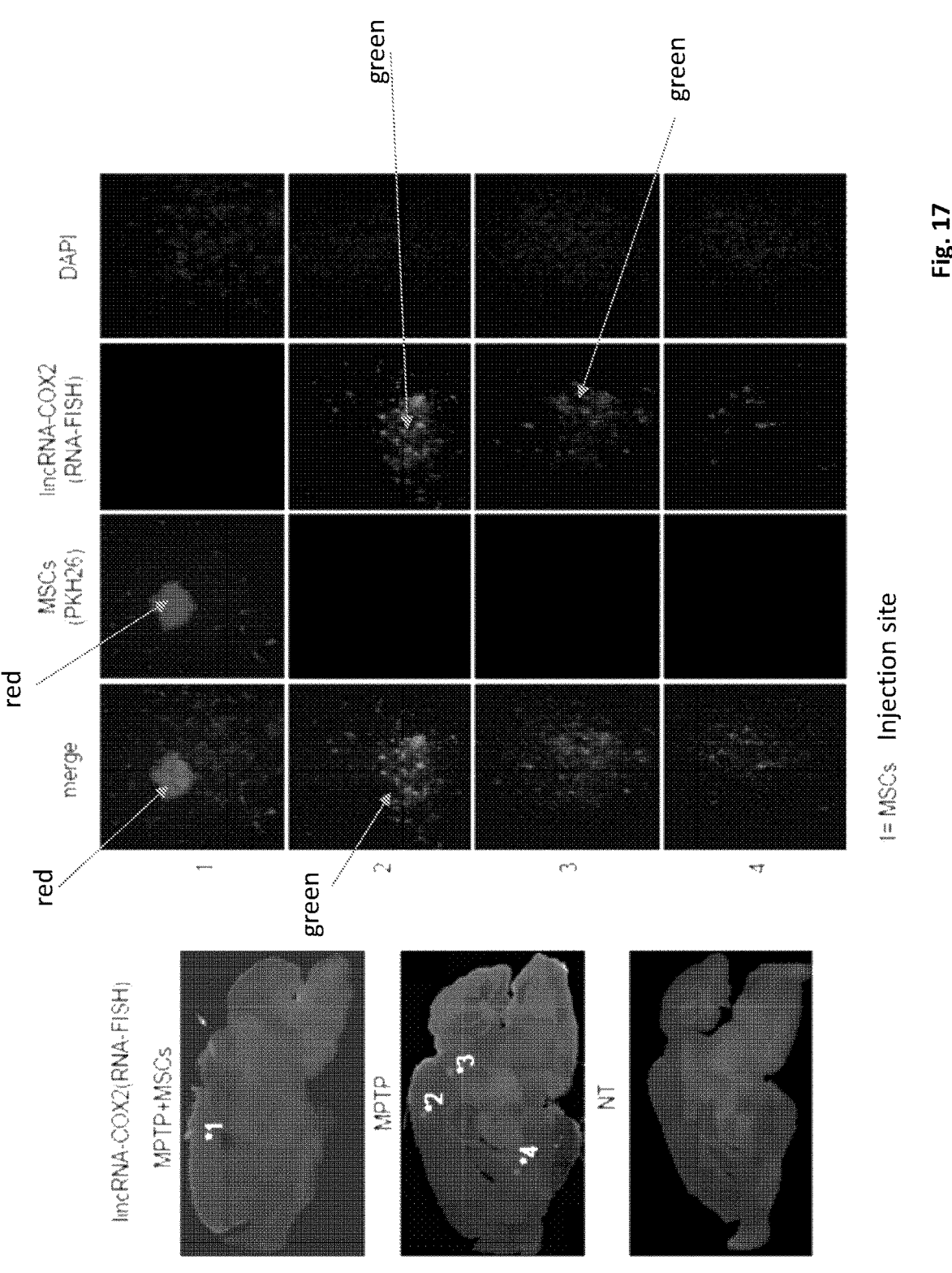
Figure 18:
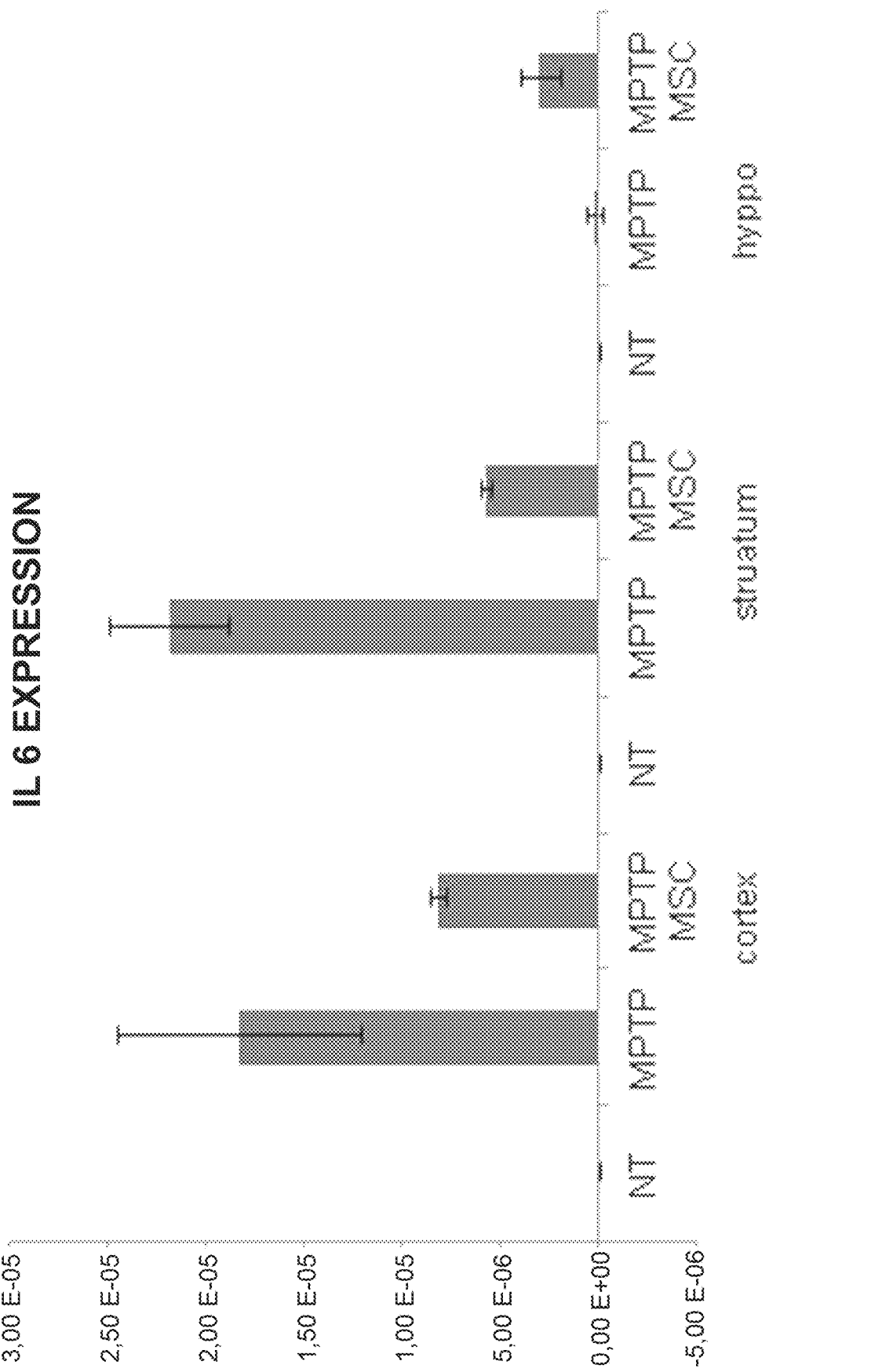
Figures 19A, 19B:
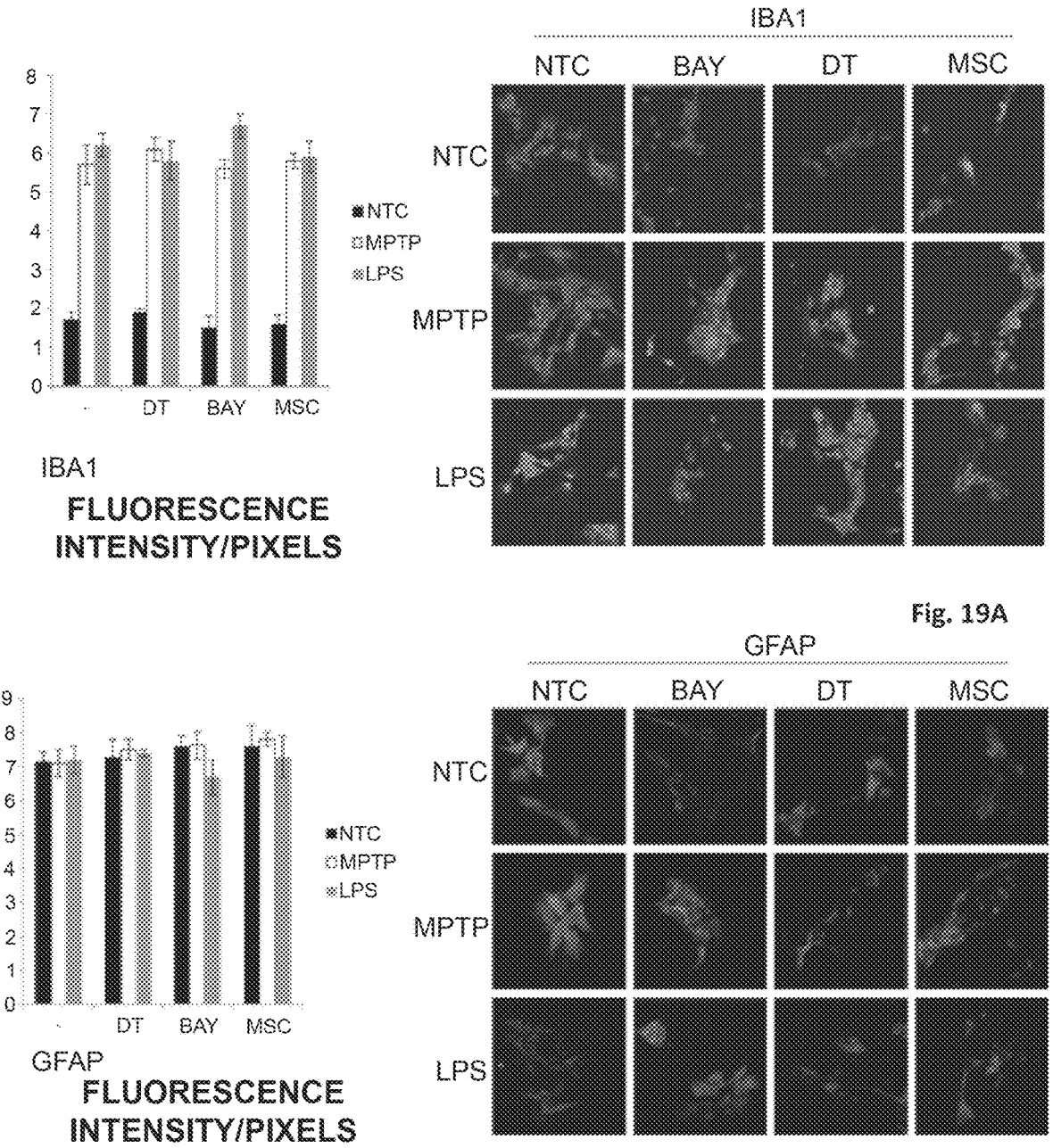
Figure 20:
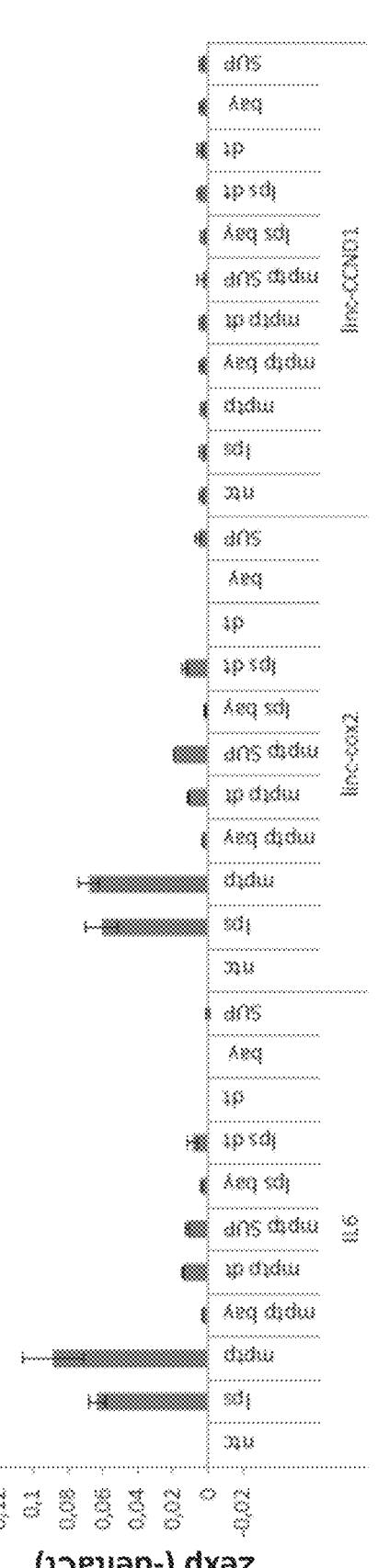
Figure 21A:
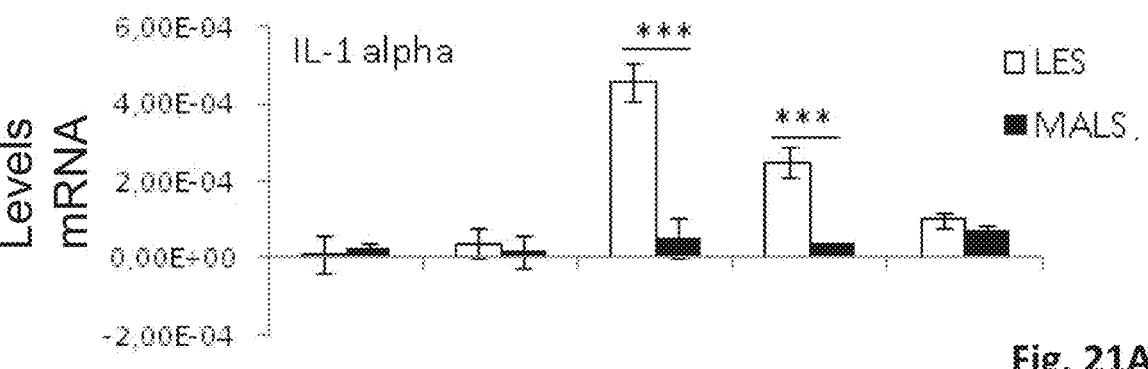
Figure 21B:
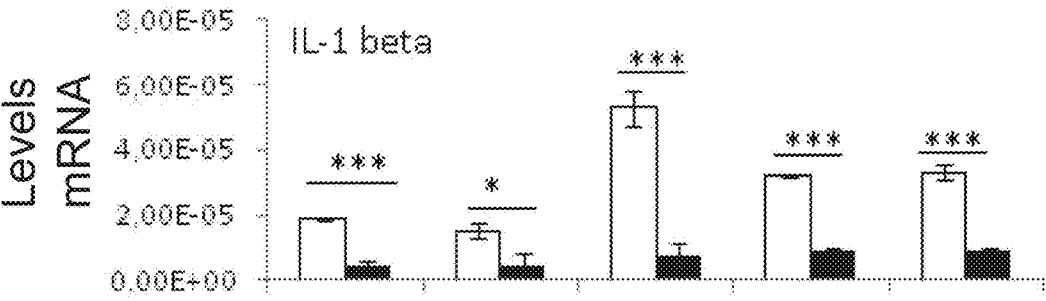
Figure 21C:
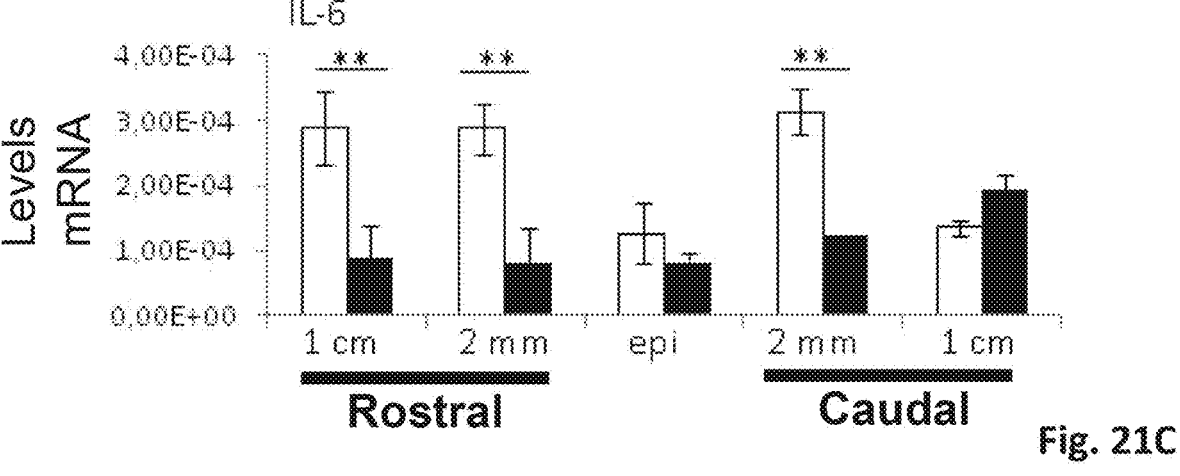
Figure 22:
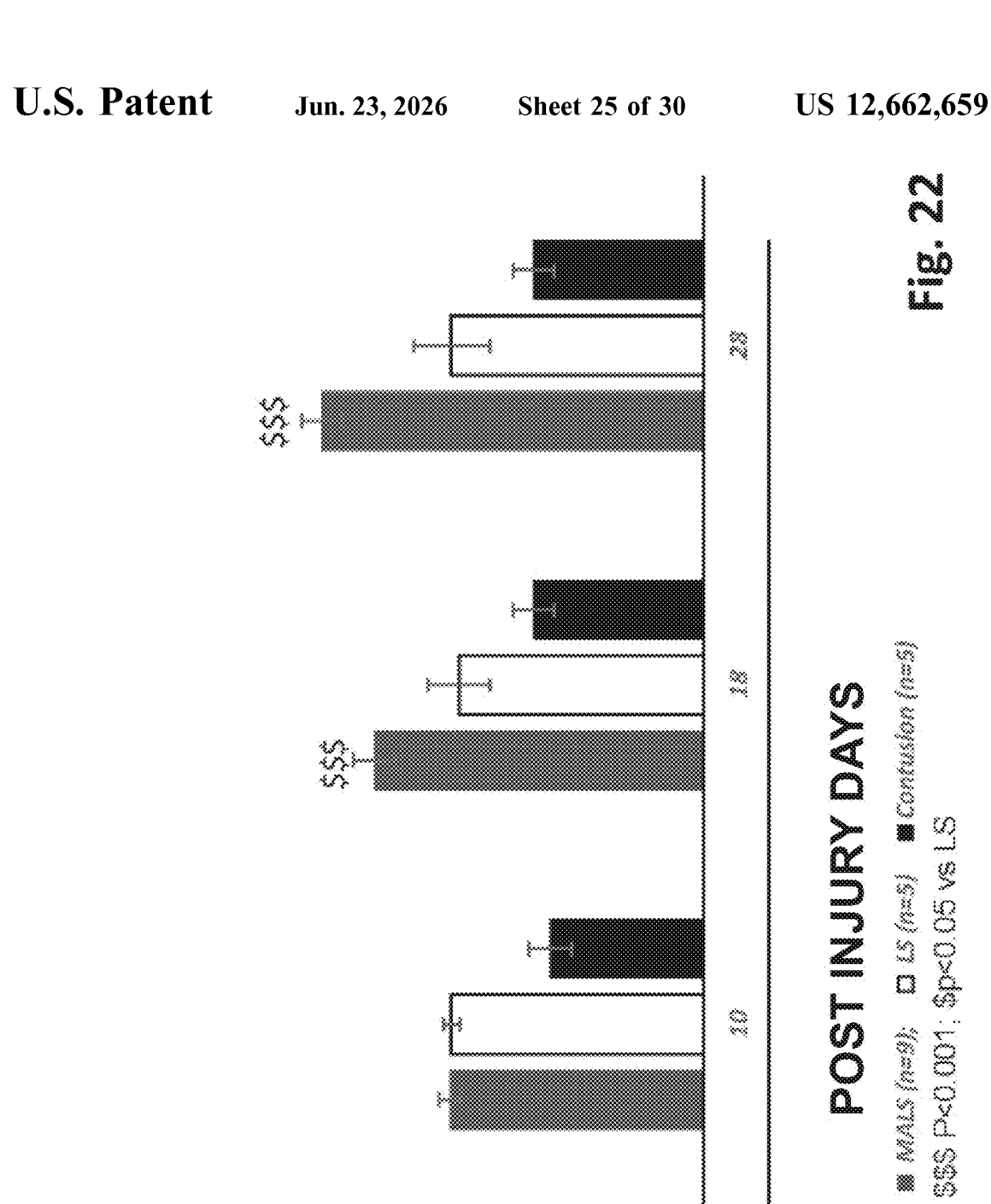
Figure 23:
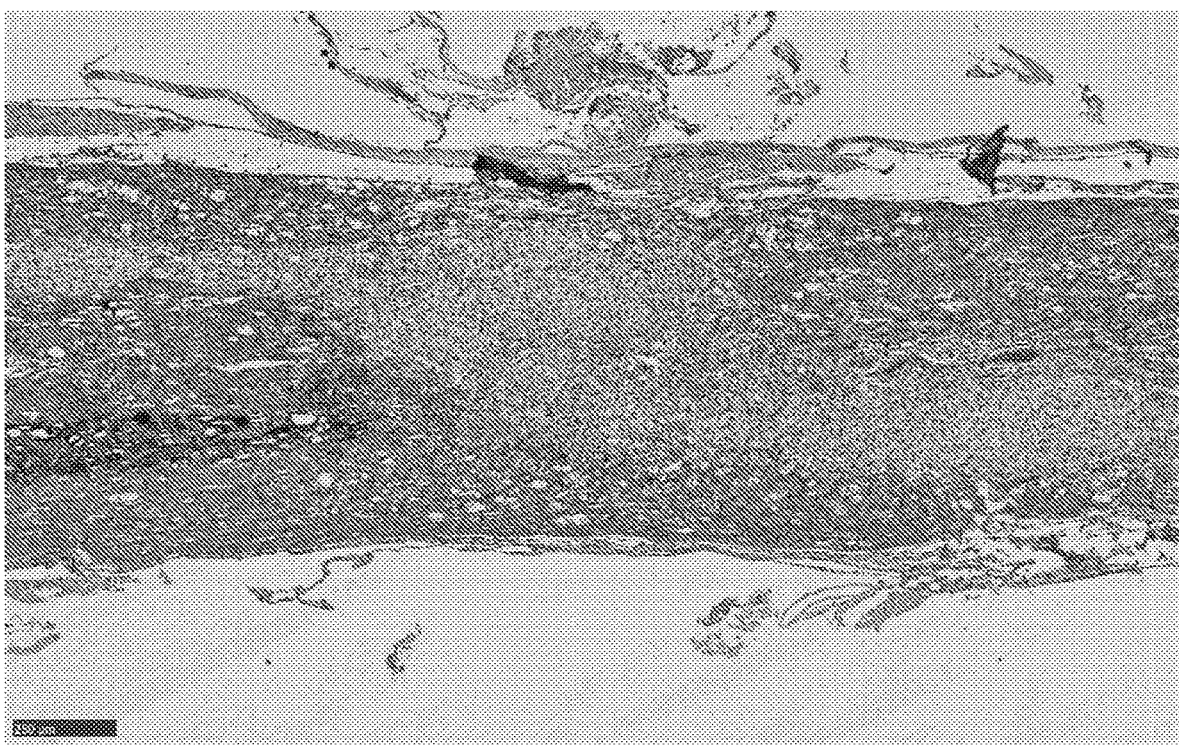

FIGS. 8A and 8B are the analysis of the karyotype unchanged in hADSCs (passages 2 to 9) obtained from adipose tissue treated with mechanical force according to the present invention. The micrograph relates to hADSCs of a case and it is representative of the same analysis performed in other three cases; PZ59=patient 59;

FIG. 9 shows the spheroids formed by hADSCs derived from adipose tissue mechanically activated according to the present invention, after having been cultured in a neurosphere medium for 21 days; NPCs=Adult murine neural precursor cells;

FIG. 10 shows that SOX2 interacts with the promoter of specific genes (bTUBIII=beta-tubulin III, TSG6, IL15=interleukin 15 and TNF-α=tumor necrosis factor-alpha) also in mesenchymal stem cells (hADSCs) isolated from adipose tissue treated with force 97×g;

FIG. 11 shows that mesenchymal stem cells (MSCs) isolated from adipose tissue mechanically activated according to the present invention (hADSCs) are able to reduce the release of IL-1 beta from THP1 cells; LPS=bacterial lipopolysaccharide endotoxin;

FIG. 12 shows that hADSCs isolated from adipose tissue mechanically activated according to the present invention efficaciously reduce the release of IL-1 beta from THP1 cells that have a LPS-mediated increase, unlike those from lipoaspirate (LS);

FIG. 13 shows the levels of mRNA of proinflammatory and anti-inflammatory cytokines. The experiment was performed by real-time RT-PCR. Results are the mean of two different experiments of real-time RT-PCR. hADSCs from mechanically activated adipose tissue knock down inflammatory cytokines IL1α and TNF-α=tumor necrosis factor-alpha and increase TSG6;

FIG. 14 shows the evaluation of the percentage of errors in the use of forelimbs. Such data were obtained by using the horizontal grid test. hADSCs obtained by the method according to the present invention reduce the percentage of error in Parkinson's animal model after transplantation;

FIG. 15 shows the evaluation of the time necessary to climb down from the top of the vertical grid in the vertical grid test. MPTP-treated mice employed longer time to turn head down and to climb down from the vertical grid. Time is considerably reduced by the intrastriatal injection of hADSCs obtained by the method according to the present invention;

FIGS. 16A-16D are the expression of lncRNA-COX2 in areas of the brain of mice. The expression was studied 4 days after intrastriatal injection of hADSCs obtained by the method of the present invention in mice with Parkinson's disease induced by MPTP. MPTP causes the appearance of Linc-COX2 in cortex and striatum (areas involved by MPTP-induced Parkinson's disease), that is eliminated by the intrastriatal treatment of the mouse with mesenchymal stem cells from adipose tissue activated according to the present invention. This is related to the improvement of the limb function;

FIG. 17 is the localization in the brain of LnRNA COX2 in health mouse (NT); in mouse suffering from Parkinson's disease (MPTP) and in mice with Parkinson's disease treated by hADSCs obtained by the method of the present invention (MPTP+MSCs). The analysis was performed 4 days after intrastriatal injection of hADSCs. LnRNA-COX2 is shown in green color and hADSCs in red color (marked with PKH26);

FIG. 18 is the expression of IL-6 mRNA: mice suffering from Parkinson's disease (MPTP) and mice with Parkinson's disease treated by hADSCs obtained by the method of the present invention (MPTP+MSCs). The analysis was performed 4 days after intrastriatal injection of hADSCs and shows IL-6 being knocked down;

FIGS. 19A and 19B are the treatment by MPTP and LPS-activated primary microglial cells;

FIG. 20 is the real-time RT-PCR of IL6 mRNA, 1nRNA COX2 and In RNA CCND1 (used as negative control) of microglia in culture and treated with LPS or MPTP. The culture medium that has been exposed to hADSC cells obtained from activated fat (SUP), knocks down the production of IL-6 and Ln-Cox2;

FIGS. 21A-21C are the anti-inflammatory action with cytokines being knocked down exerted by the tissue of the present invention in spinal cord at 48 hours from the traumatic injury;

FIG. 22 is the functional recovery (BMS scale) of hind limbs in mice with spinal injury transplanted with lipoaspirated adipose tissue (LS) and with adipose tissue mechanically activated according to the present invention (MALS) compared with a saline treatment. MALS promotes a progressive and significant functional recovery;

FIG. 23 is the graft in the injured spinal cord of adipose tissue mechanically activated according to the present invention.

Figure 24:
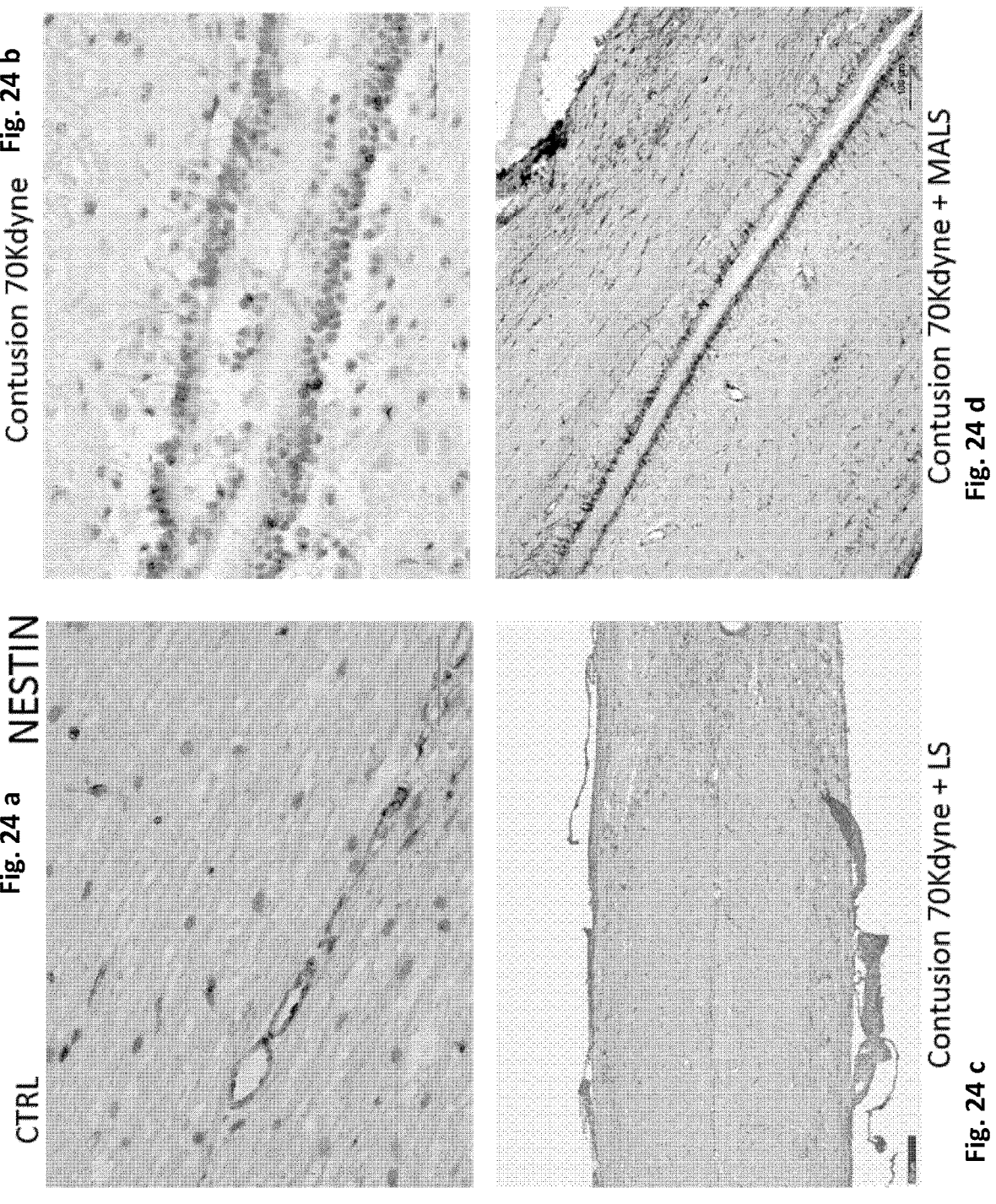
Figure 25:
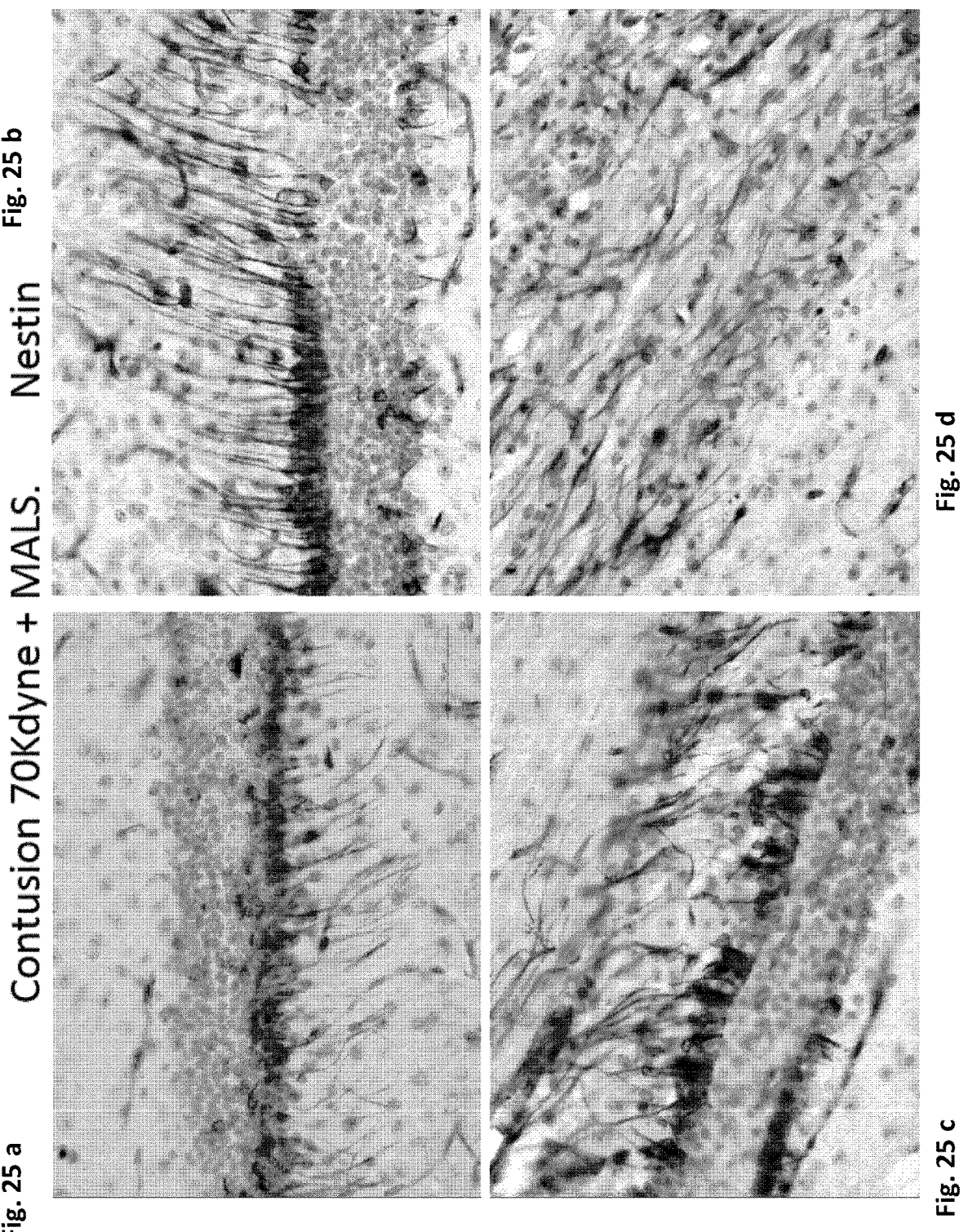
Figure 26:
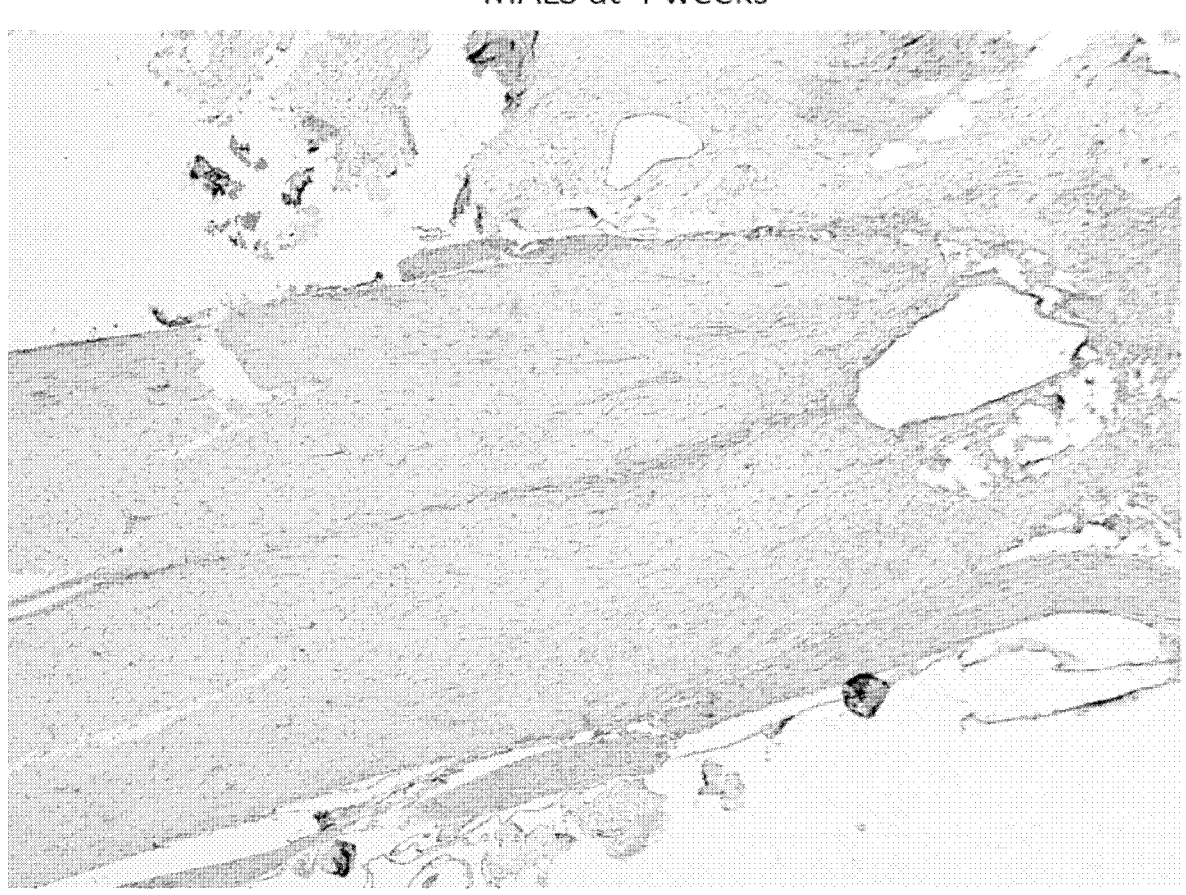
Figures 27, 27B:

FIG. 24 is the treatment of a traumatic injury at 70Kdyne of the spinal cord, FIG. 24a a control of the expression of Nestin without treatment, FIG. 24b the contusion at 70Kdyne, FIG. 24c the contusion at 70Kdyne+LS and FIG. 24d the contusion at 70Kdyne+MALS respectively;

FIGS. 25a to 25d are enlarged details of ependymal stem cells activated by activated adipose cells that is application of MALS;

FIG. 26 is the situation after 4 weeks from the activation by MALS;

FIGS. 27a to 27c are the formation of new neurons in the grey matter of the injured spinal cord due to migration of ependymal stem cells activated by MALS.

The method of the present invention allows adipose tissue removed from the human body to be mechanically activated, particularly mesenchymal stem cells present therein.

According to one of the known techniques, the adipose tissue to be processed by the method of the present invention can be obtained by elective liposuction procedures under local anesthesia.

The final product will be called as lipoaspirated adipose tissue (lipoaspirate).

It is obviously possible to use also other procedures for extracting adipose tissue.

In the present description reference is made to human adipose tissue but obviously the method of the present invention can be applied also to animal adipose tissue.

An example of a procedure involves an infiltration step, where a saline solution containing the vasoconstrictor epinephrine (2 mg/ml) is infused in the adipose tissue to minimize blood loss and contamination of the tissue by cells of peripheral blood.

According to one embodiment of the present invention, for mechanical activation, 10 ml of washed lipoaspirated adipose tissue was harvested in a 50 ml tube and subjected to orbital shaking with a force equal to 97×g for different time that is 3, 6, 10 and 20 minutes, at ambient temperature.

According to the present invention the anti-inflammatory properties of the adipose tissue, particularly of human adipose tissue containing mesenchymal stem cells, can be activated by applying a specific movement, having a specific force (intensity) and duration.

Considering that accumulation of adipose tissue is actually considered as an inflammatory process, proinflammatory and anti-inflammatory factors have been evaluated in lipoaspirated adipose tissue obtained by the same group of patients and subjected to specific mechanical forces for a variable amount of minutes.

The non processed lipoaspirated fat was used as control.

Such as shown in FIG. 1, the protein TSG6 is already observable after 3 minutes of stimulation and it has the maximum expression within 6-10 minutes; TNF-alpha is suppressed in 6 minutes.

Experimental results show that the application of a force of 97×g ("×g" that is, as known, a multiple of the gravitational force of the Earth):

eliminates the typical expression of adipose tissue of inflammatory cytokines such as tumor necrosis factor-alpha (TNF-alpha);

considerably enhances its natural inhibitor TSG6 and interleukin 15, that are present at marginal level in the normal adipose tissue that is not processed tissue, considerably improves the expression of leptin, the suppressor of the desire for food produced by fat.

Said improved expression of leptin proves that said force can be also applied in vivo on the surfaces of the body where said hormone plays an important role.

Figure 1A:
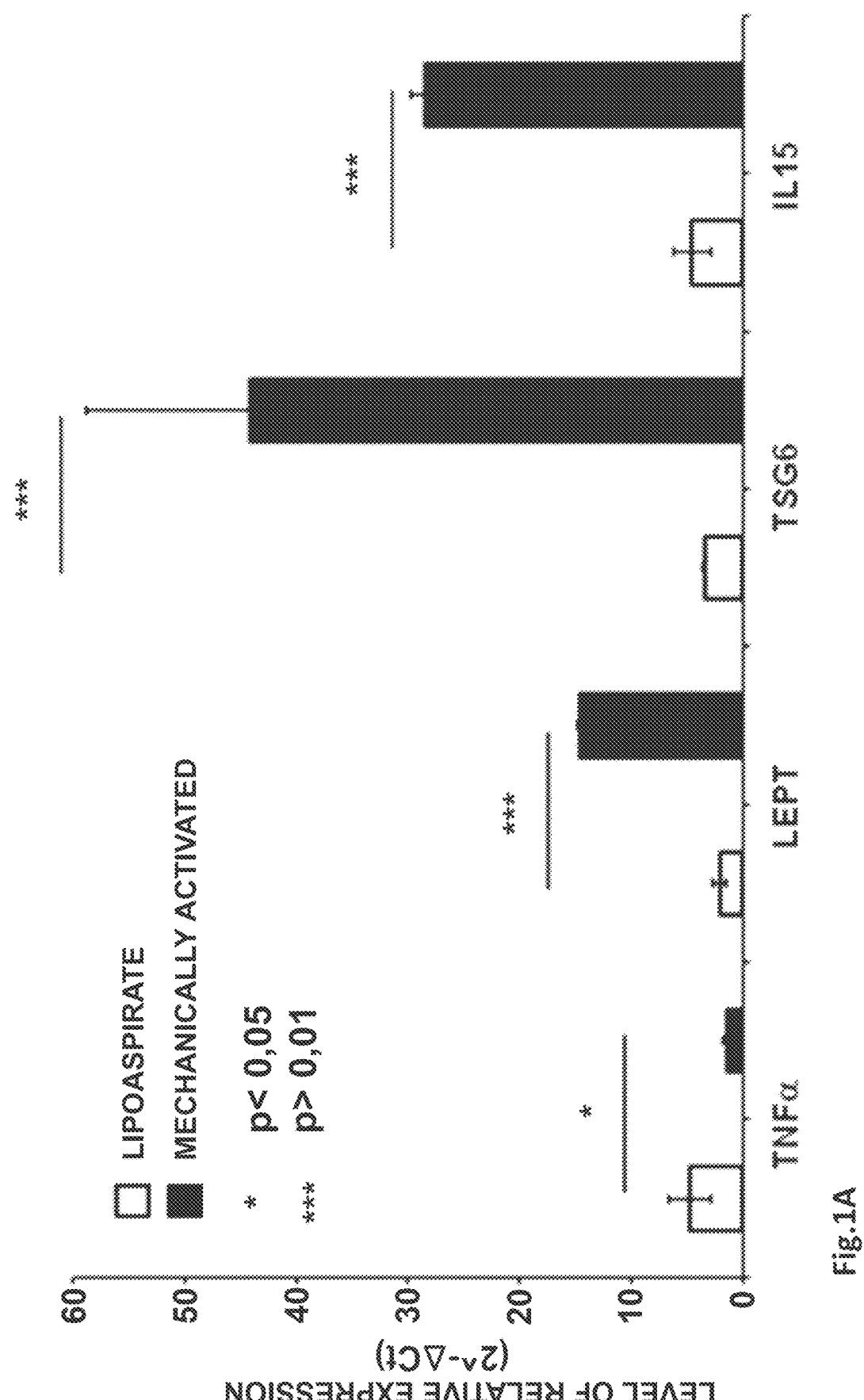
Figure 1B:
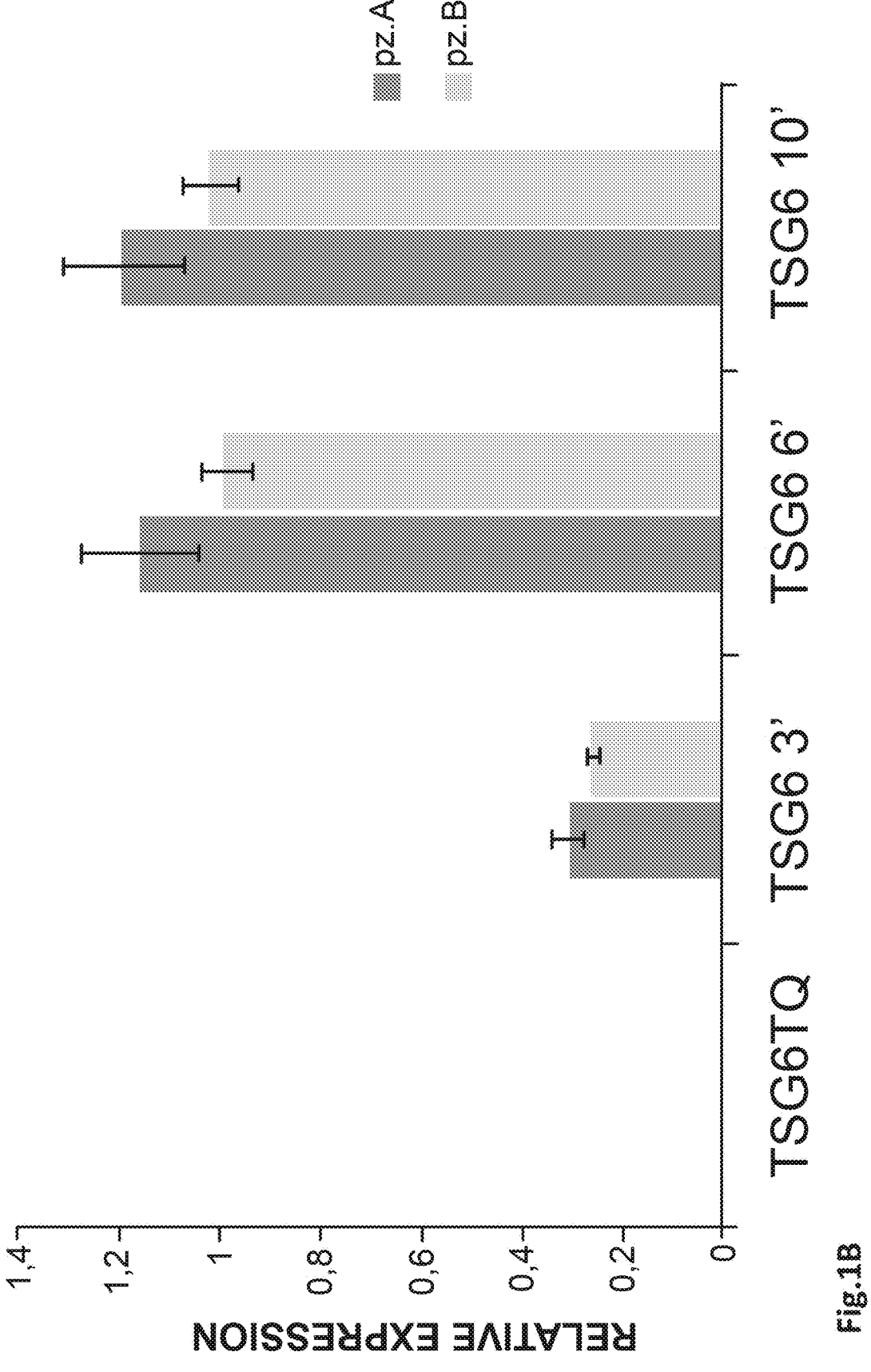
Figure 1C:
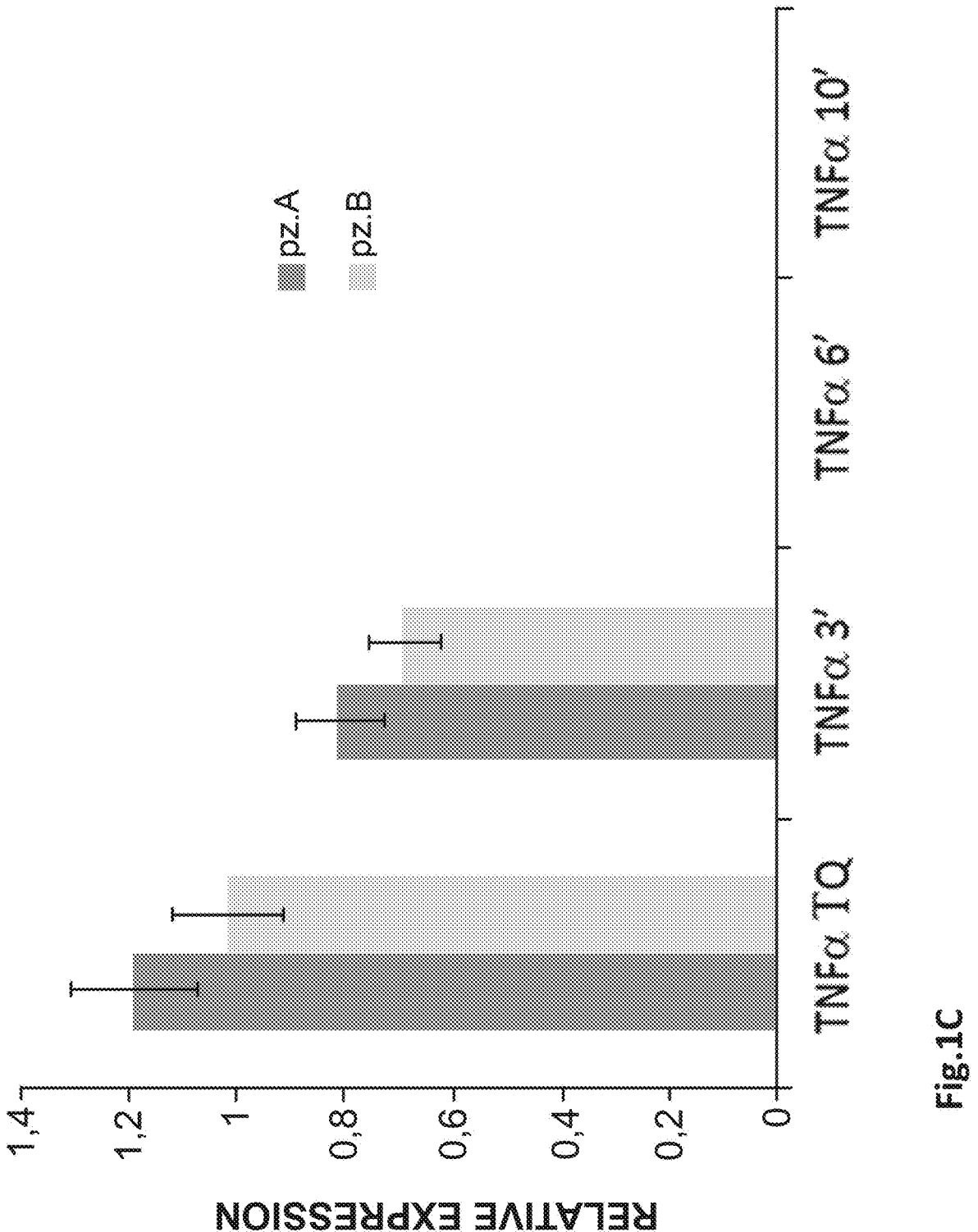

With reference to FIG. 1 data show that:

the maximum expression of TSG6 is reached within 6 and 10 minutes of mechanical activation with force 97×g (FIG. 1b), the production of TNF-alpha is inhibited within 6 minutes in the same conditions (FIG. 1c).

Moreover the maximum expression of beta-tubulin III is reached within 20 minutes of mechanical activation with force 97×g.

Lower forces are less efficacious.

According to the present invention in order to achieve a promotion of anti-inflammatory properties and an improvement of repair capacity of the lipoaspirated adipose tissue it is possible to apply a force with intensity ranging from 40 to 120×g.

Figure 1D:
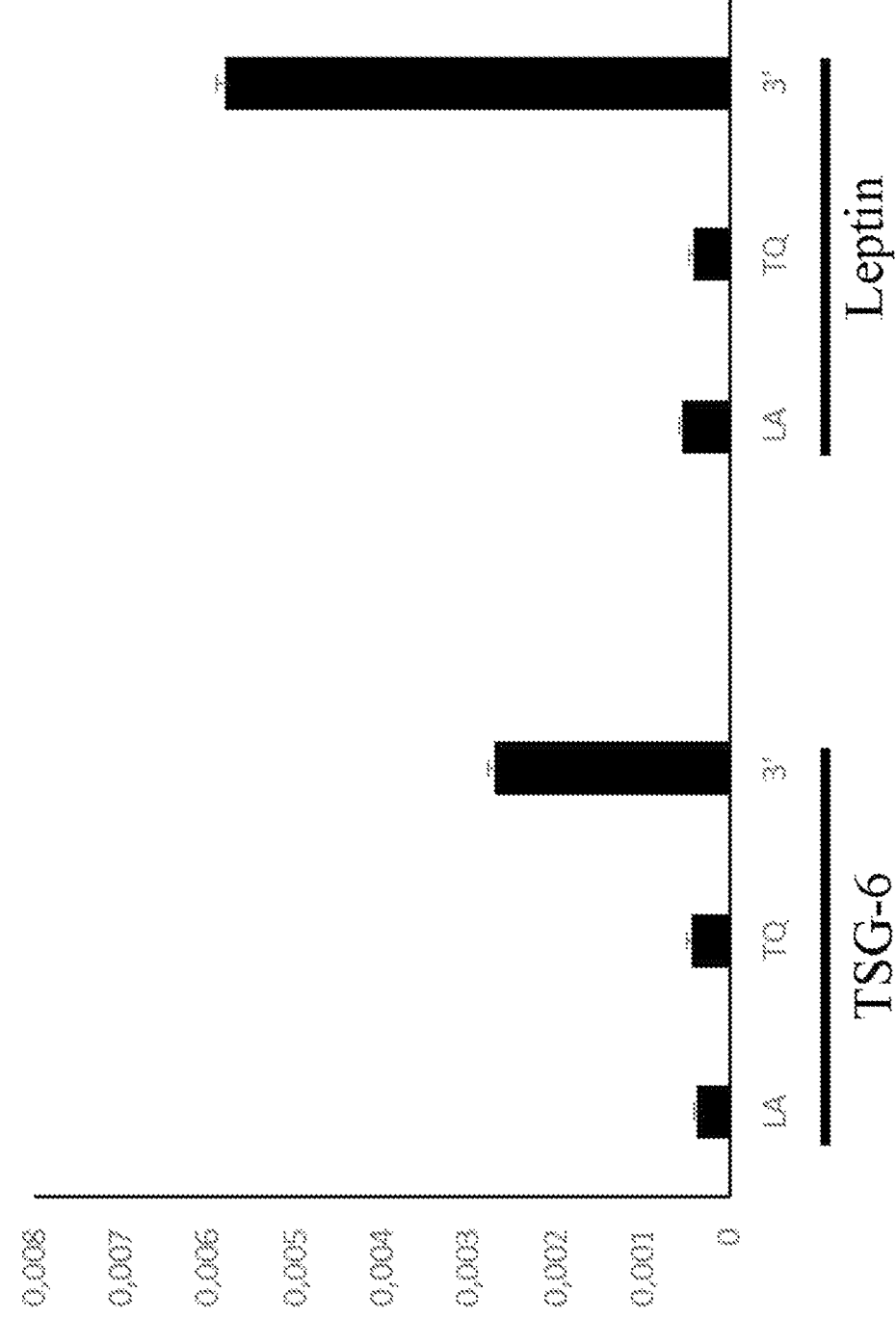

The mechanical activation of anti-inflammatory processes is efficacious even when the adipose tissue is cryopreserved at −80° C. for several months, such as shown in FIG. 1D.

When the force 97×g is applied for three minutes on the adipose tissue that has been cryopreserved, TNF-alpha is cancelled while TSG6 and leptin considerably increase as in fresh tissue.

The simple lipoaspiration procedure produces a soft mechanical activation that is observed by the expression of some pluripotency-related genes (SOX2, OCT4, Nanog), of beta-tubulin III and of TSG6 mRNA, as determined by real-time RT-PCR.

Figure 2:
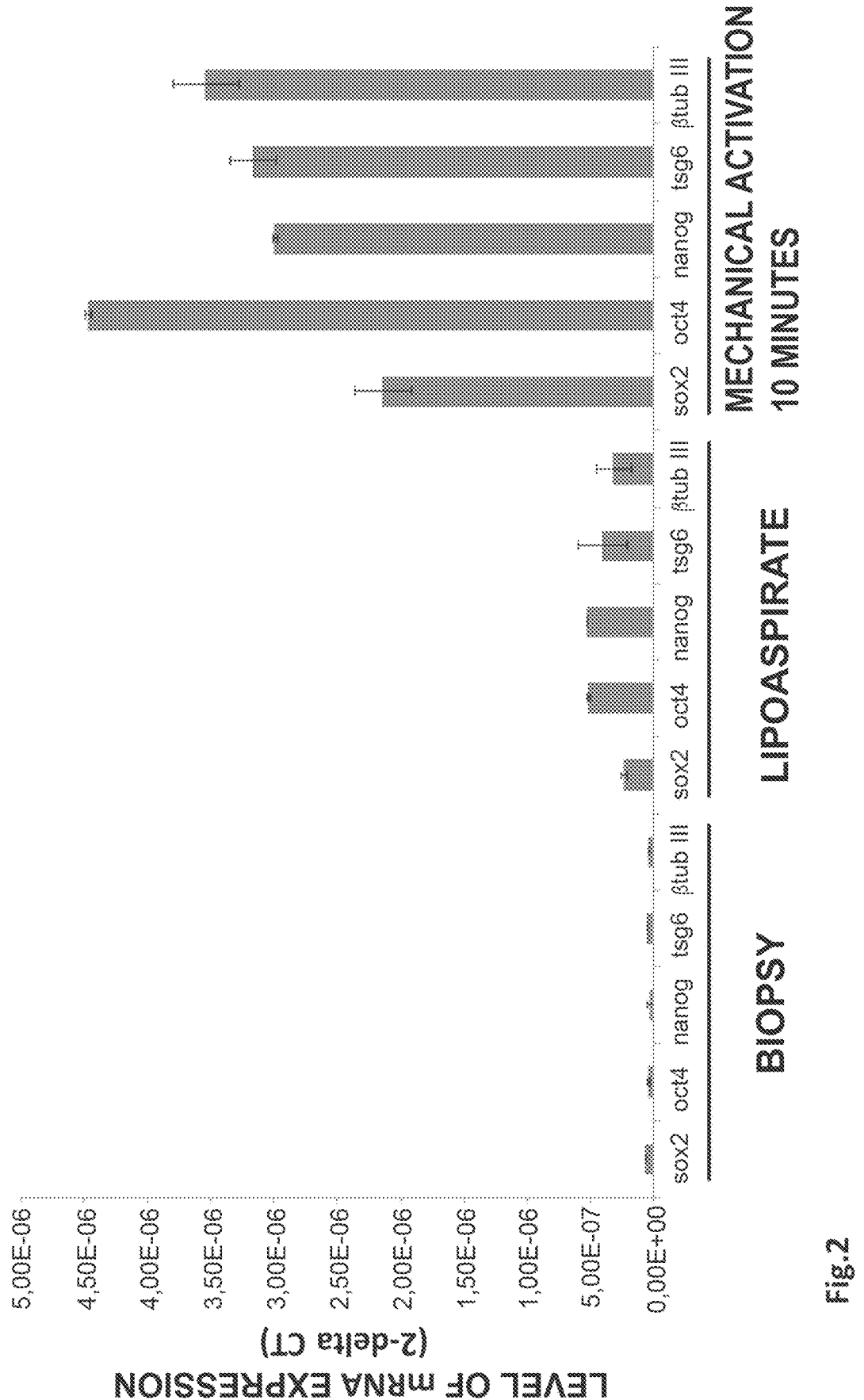

The results obtained in the human adipose tissue from biopsy, in lipoaspirated human adipose tissue, and human adipose tissue lipoaspirated and mechanically activated (10 minutes) are shown in FIG. 2.

FIG. 2 shows the expression of pluripotency genes (SOX2, OCT4, Nanog), beta-tubulin III and TSG6 tested with real-time RT PCR in samples from biopsy of human adipose tissue, lipoaspirated and lipoaspirated mechanically activated by the method of the present invention (10 minutes). All the investigated genes are hardly activated in the regular bioptic tissue, that is non processed tissue, according to the present invention (biopsy), and are slightly activated by performing the known Coleman procedure after liposuction (lipoaspirate). Differently the upregulation is incomparably higher after the specific activation according to the present invention for 10 minutes.

All the investigated genes are hardly active in the regular bioptic tissue, not mechanically manipulated according to the present invention, and such activation is slightly improved by the known Coleman procedure after liposuction (lipoaspirate). However the application of the specific mechanical force, here described and claimed, for 10 minutes causes an incomparably higher up-regulation.

Pluripotency regulator genes SOX2, NANOG and OCT4 are completely activated within 6 minutes of mechanical activation with force 97×g.

Figure 3:
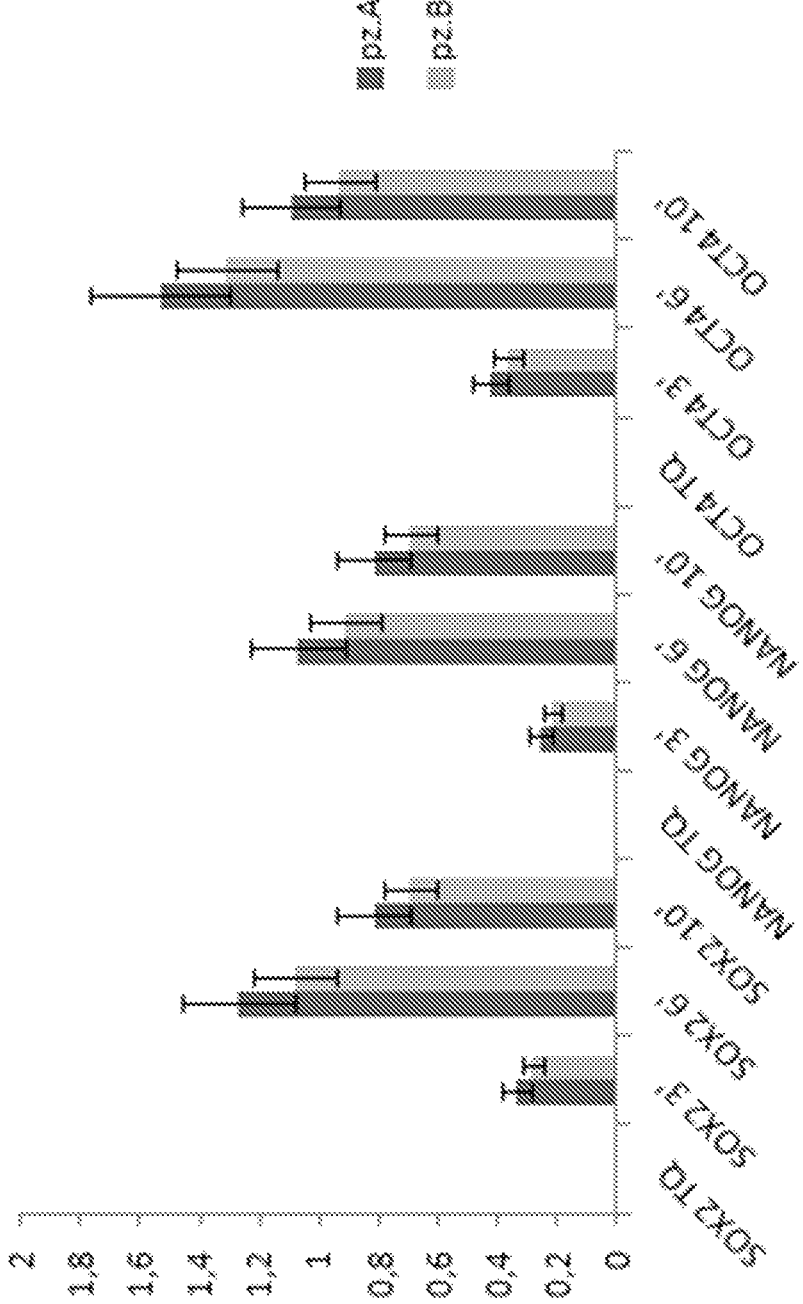
FIG. 3 is the results of a real-time quantitative PCT measuring the expression levels of mRNA of pluripotency genes; TQ=time 0, PZA=patient A, PZB=patient B.

Therefore in addition to anti-inflammatory properties, also the parameters that define stemness of mesenchymal stem cells present in the adipose tissue are increased by the mechanical activation, in a manner independent from force and time (FIG. 3).

It is known that Sox2 has a critical role in the maintenance of embryonic and neural stem cells.

Furthermore it has been noted that (Go et al., 2008) Sox2 is not only essential for pluripotency and self-renewal of embryonic stem cells, but is also expressed in somatic stem cells with superior expansion and differentiation potential (Vai et al., 2008).

Sox2 is a transcription factor (34 kDa) containing a HMG box for DNA binding and it forms trimeric complexes with Oct4 controlling the expression of a given number of genes.

According to the present invention the specific mechanical activation of the adipose tissue directly regulates the gene expression guided by the transcription factor SOX2 on the region of the promoter of different genes coding for the above described cytokines.

Figure 4:
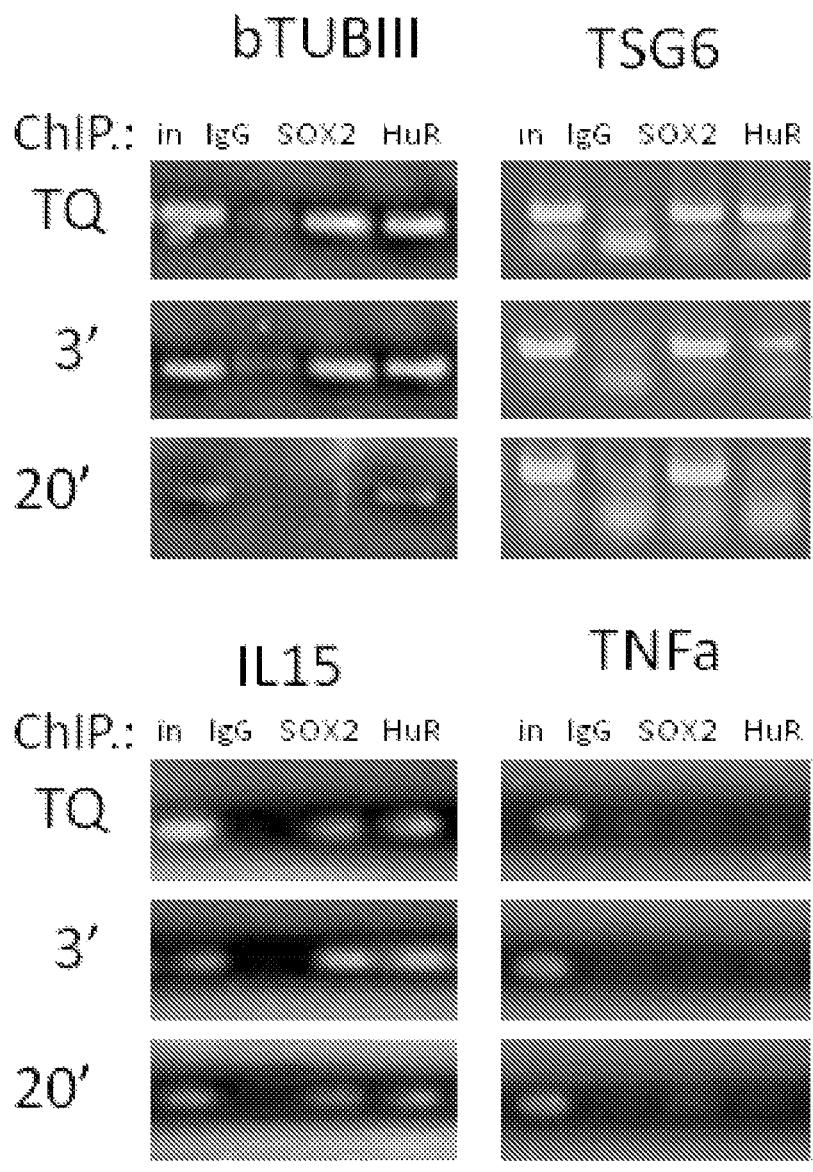
FIG. 4 shows that the application of a mechanical force to the adipose tissue modifies the interaction of SOX2 and HuR with the promoter of specific genes (bTUBIII=beta-tubulin III, TSG6, IL15=interleukin15 and TNF-α=tumor necrosis factor-alpha)

Moreover Chip-Seq on immunoprecipited SOX2 shows a high binding efficiency of SOX2 on the promoter IL-6 in glioblastoma or ES cells (Fang et al., 2011). The region of the promoter −3000 bp of beta-tubulin III, TSG6, TNF-alpha, IL1B, IL10, IL15 and leptin was analysed in silico, to search for consensus sequence for SOX2 and ChIP tests (chromatine immunoprecipitation) were designed to detect binding of the transcription factor in liquid phase. The Chip test shows that SOX2 and HuR bind to the region of the promoter of beta-tubulin III, IL15 and TSG6 and that the mechanical application of 97×g regulates in differential manner such interaction (FIG. 4).

SOX2 does not bind anymore the beta-tubulin III promoter after 20 minutes of application of the above mentioned force, therefore the transcription of beta-tubulin III is improved.

The increased transcription of TSG6 is regulated by the loss of HuR binder, while IL15 is likely regulated by other factors different from Sox2 and HuR.

Stem cells from adipose tissue were purified from human fat harvested through microliposuction under tumescent local anesthesia by Coleman microcannulas.

It is obviously possible to use also other procedures for removing the adipose tissue.

Following this procedure, the lipoaspirated adipose tissue was centrifuged in a sterile closed system at 2000 rpm for 10 minutes and the pellet was subjected to collagenase digestion for half an hour at 37° C.

The digest is centrifuged for separating the floating population of mature adipocytes from the stromal vascular fraction (SVF).

After 24 hours plating in a standard medium (Dulbecco Modified Eagle Medium supplemented with 10% fetal bovine), non-adherent cells were removed.

The plastic-adherent cell population define the stromal cells derived from adipose tissue (ADSCs).

Starting from the adipose tissue subjected to a force 97×g, an efficacious method, that avoids enzymatic treatment, and reproducible for isolation and expansion of hADSCs (human adipose derived stem cells) has been developed by modifying the methods described by Matsumoto et al., 2007 and Perrini S. et al., 2013.

The adipose tissue lipoaspirated and treated with a force of 97×g was placed in 25 cm² culture flasks (NUNC, Roskilde, Denmark) completely filled with culture medium. This allows the tissue to adhere to plate top.

After 2 weeks of culture the adipose tissue was removed, the flask turned upside down and cells were kept in culture.

Cells reached a confluence of 90% in 30 days.

The yield of cells was about 5.5-6×105 cells for each plate containing 2 ml of mechanically treated adipose tissue.

Figure 5A:
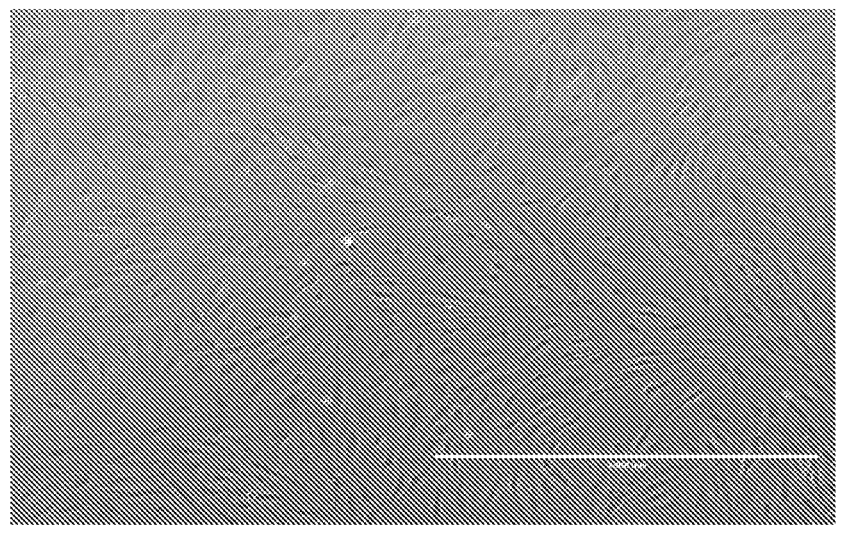
FIGS. 5A and 5B are the morphology in vivo of hADSCs obtained from adipose tissue treated by orbital shaking according to the present invention (6 and 10 minutes, respectively)
Figure 5B:
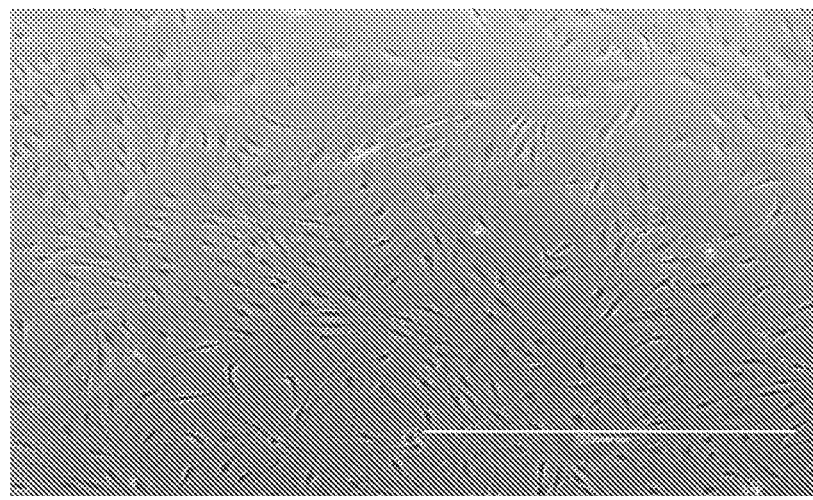

Morphology in vitro (captured by means of EVOS® microscope apparatus, AMG, USA) of these cells exhibits a fibroblast-like phenotype comparable to that of cells obtained by means of classical methods (FIGS. 5A and 5b).

Figure 6B:
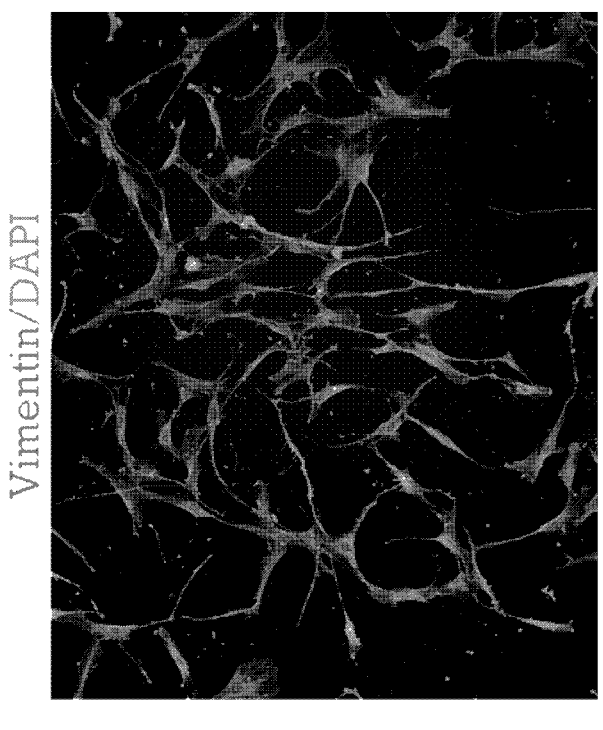
FIGS. 6A and 6B are the expression of beta-tubulin III (TUJ 1) and of vimentin in hADSCs obtained from adipose tissue mechanically treated with orbital shaking according to the present invention.
Figure 6A:
Figure 6A:
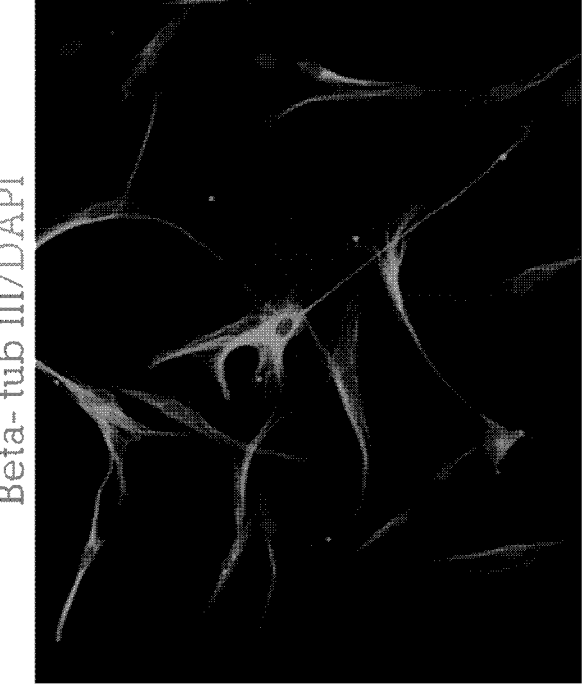
Figure 7:
FIG. 7 shows FACS analyses of the expression of mesenchymal markers in mesenchymal stem cells obtained from adipose tissue treated or not treated with a force 97×g; TQ=time 0.

Such mesenchymal stem cells have the typical expression of beta-tubulin III (TUJ1) and vimentin (FIG. 6).

hADSCs cells (human adipose derived stem cells) isolated by means of the protocol described above express mesenchymal markers according to FACS analysis (FIG. 7) with high values (90-100%) for the known typical mesenchymal markers (such as CD44, CD73, CD90 and CD166), a mean value for endothelial tissue (CD31, CD34, CD144, CD146, KDR) and a minimal representation for hematopoietic tissue (CD45, CD133, CD56) (FIG. 7). This can suggest that these cells can also be subjected to endothelial fate.

In order to study the chromosomal stability of hADSCs obtained from the adipose tissue mechanically activated according to the present invention, a QFQ banding has been carried out. Cells did not present any chromosomal rearrangement and the chromosome number was normal in 9 passages in culture (FIGS. 8A and 8B).

The generation of spheroids is normally limited to neural stem cells, here it has been demonstrated that also hADSCs from fat activated according to the present invention form neurospheres.

hADSCs (human adipose derived stem cells) were incubated with serum-free medium usually used for forming neurospheres (Gritti et al., 2002).

The test forming the spheres was carried out with 5×103/ cm$^2$ plating. About 50% of hADSCs obtained from mechanically activated adipose tissue, according to the present invention, formed large spheroids reaching an average diameter of 100 micron at 21 culture days (FIG. 9).

About 50% of hADScs obtained from mechanically activated adipose tissue formed large spheroids reaching an average diameter of 100 micron at 21 culture days, and forming a mean of 100.95±10.89 spheres/cm$^2$ within 21 days (FIG. 9).

Adult murine neural precursor cells (NPCs) obtained from the subventricular zone were used as positive control: in this case the formation of spheres was obviously higher (FIG. 9).

The involvement of SOX2 in the regular expression of cytokines mentioned above was also studied in cells isolated from adipose tissue treated with a force 97×g.

Chip assay shows that SOX2 binds with the promoting region of beta-tubulin III, IL15 and TSG6 (FIG. 10). Thus the activation in vivo is maintained also by hADSCs derived from the method of the present invention.

Recent reports suggest that MSCs (Mesenchymal stem cells) are able to modulate inflammation (Prockop et al., 2013).

THP-1 is a category of rounded and single cell suspension, with distinct monocytes markers resembling primary monocytes and macrophages in morphology and differentiation property (Tsuchiya et al., 1980).

Interleukyn-1β (IL-1β) is a powerful mediator of inflammation and immune response, mainly produced by activated monocytes (Dinarello 1994).

The stimulation of monocytes with bacterial lipopolysaccharide endotoxin (LPS) leads to the production of IL-1β by activation of the pro-IL-1 gene, expression of pro-IL-1β mRNA, and following translation of pro-Il-1β message.

Pro-IL-1β is processed to the mature and biologically active IL-1β of the cysteine protease interleukin-1 converting enzyme (Kostura et al., 1989).

Anti-inflammatory action of hADSCs obtained from mechanically activated adipose tissue was evaluated in a co-culture test (Trans-Well®) with THP1 cells activated with LPS (10 micrograms/ml; for 3 hours).

As shown in FIG. 11 the release of IL-1β is maximum after 3 hours from the stimulation with LPS, and the presence of hADSCs obtained from mechanically activated adipose tissue considerably reduced the secretion of chemokine (FIG. 11).

A similar experiment based on the release reaction of IL-1beta from THP1 monocytes activated by LPS ((10 micrograms/ml; for 3 hours) (CTRL+) was performed to compare the action of hADSCs obtained from activated adipose tissue (cell 10) with those from lipoaspirated adipose tissue (LS).

FIG. 12 shows that THP1 releases IL-1beta and such release is doubled by the addition of LPS. The increase in the release of IL-1beta is eliminated by mesenchymal stem cells derived from adipose tissue mechanically activated according to the method of the present invention, while those from lipoaspirate have a negligible marginal effect (FIG. 12).

Anti-inflammatory activity of hADSCs from activated adipose tissue according to the method of the present invention is also highlighted from the following experiments shown below.

FIG. 13 shows that monocytes activated by LPS (THP1+ LPS) express high levels of inflammatory cytokines, also in presence of stem cells derived from lipoaspirate (LS); such levels drastically are reduced when such monocytes are cultured in presence of hADSCs obtained from adipose tissue mechanically activated by the method of the present invention (FIG. 13). It also demonstrates that the production of anti-inflammatory peptide TSG6 is strongly implemented by hADSCs derived from adipose tissue activated by the method of the present invention.

The present invention relates to hADSCs that is mesenchymal stem cells obtained from human or animal adipose tissue mechanically activated by the method of the present invention for the use as a medicine.

In particular they are applied in cell therapy both for human beings and for animals.

The present invention relates also to hADSCs that is mesenchymal stem cells obtained from human or animal adipose tissue mechanically activated by the method of the present invention for the use in the treatment of motor or coordination disorders, for example in patients suffering from Parkinson's disease.

The recovery of motor dysfunctions, in a Parkinson's disease model was investigated by means of horizontal and vertical grid tests ("horizontal grid test" and "vertical grid test").

The graph shown in FIG. 14 shows that mice rapidly loose coordination of forelimbs and hind limbs, after exposition to MPTP, such dysfunction is consolidated at 10$^{th}$ day post-injury, when the cell intrastriatal graft is performed.

3 days after the transplantation (13$^{th}$ day) hADSCs obtained by the method of the present invention already cause a gradual improvement in limb coordination, showing a decrease in the percentage of movement errors of forelimbs, that after 10 days is 60-70% in MPTP animals and about 25% in animals treated with hADSCs obtained from adipose tissue mechanically activated by the method of the present invention.

These positive results were observed also by performing the "vertical grid" test.

A considerable longer time was detected in MPTP treated mice with respect to the control (FIG. 15) for turning around and climbing down on the vertical grid.

Mice treated with hADSCs obtained from adipose tissue mechanically treated by the method according to the present invention show an improvement already 3 days after the injection (FIG. 15).

Performances of animals considerably improved also in the following days.

It is known that microglia cells, the resident innate immune cells in the brain, have been implicated as active contributors to neuron damage in neurodegenerative diseases, in which the overactivation and dysregulation of microglia might result in disastrous and progressive neurotoxic consequences.

Inflammation is a base component of a wide range of neurodegenerative diseases and of their associated neuropathology, and more and more evidences suggest that microglia is a causal key factor in such process.

Activated microglia is present close to degenerating neurons in substantia nigra of patients suffering from Parkinson's disease and patients suffering from other Parkinsonian disorders (McGeer et al., 1988, Langston et al., 1999, Inamura et al., 2003).

Activation of microglia in such disease is not limited to substantia nigra, but it is found also in putamen, hippocampus, transentorhinal cortex, cingulate cortex and temporal cortex (Inamura et al., 2003).

The selective loss of dopaminergic neurons (DA) in substantia nigra may be due to many negative events, such as depletion of glutathione for dopaminergic neurons (resulting in a reduced antioxidant effect), high content of DA (redox active molecule) in neurons of substantia nigra (Zigmund et al., 2002), high iron concentrations (Zecca et al., 2004) (redox active elements) and an increase of microglia in substantia nigra (Lawson et al., 1990) with respect to other regions.

Therefore dopaminergic neurons in substantia nigra could be particularly vulnerable to inflammatory attacks due to their precarious redox balance and colocalization with a large microglia population.

The transplantation in mice of hADSCs obtained from adipose tissue mechanically activated by the method of the present invention changes the genetic profile of mouse brain.

Particularly the effect of transplantation on the regulation of long non-coding RNA involved in inflammatory processes, such as lincRNA-Cox2 was observed (Gomez et al., 2013).

The mammalian genome "junk DNA" encodes many thousands of large non-coding transcripts, including a class of large intergenic non-coding RNAs (lincRNAs), few among them have been functionally characterized for their biological role by Guttman and contributors (Guttman et al., 2011) that performed loss-of-function studies on lincRNAs expressed in mouse embryonic stem cells (ESCs) and characterized the effects on gene expression.

Recent studies have found thousands of long non-coding RNAs (LncRNAs) in mammalian genomes (Birney et al., 2007, Guttman et al., 2009-2012) that regulate the gene expression in different biological processes (Guttman et al., 2011). LncRNAs are differentially regulated in virus-infected cells and in dendritic cells following lipopolysaccharide (LPS) stimulation.

The lincRNA-COX2 expression was studied by RT-PCR, in a different area of the brain (cortex, striatum, hippocampus of animals with MPTP-induced Parkinson's disease and 4 days after injection of stem cells). The expression of lncRNA-COX2 is induced in mice suffering from Parkinson's disease and its expression seems to be related with the presence of HuR as demonstrated by its co-immunoprecipitation in RIP assay (RNA immunoprecipitation) performed on homogenized striatum.

The expression of lncRNA-COX2 is deeply down-regulated by intrastratial injection of hADSCs obtained from adipose tissue mechanically activated by the method of the present invention (MPTP/MSC; FIG. 16A-D). Down-regulation of lncRNA-COX2 is strictly related to the recovery of the function by the animal, such as shown by behavioral tests (FIGS. 16A-D).

The expression of lncRNA-COX2 was investigated also by FISH (Fluorescent in situ hybridization) an approach able to detect and localize specific RNA targets (mRNA, lncRNA and miRNA) in cells, circulating tumor cells, and tissue samples (FIG. 17).

Recently it has been demonstrated that linRNA COX2 up-regulates the expression of IL-6, by acting on its promoter (Carpenter et al., 2013).

Levels of expression of IL-6 mRNA have been studied by real-time RT-PCR in cerebral areas of mice suffering from Parkinson's disease and mice affected by Parkinson's disease treated by hADSCs of the present invention.

As shown in FIG. 18 the expression of IL-6 is considerably increased and it is deeply opposed by the intrastriatal injection of hADSCs of the present invention.

The mechanism with which hADSCs can down-regulate the expression of lincRNA-COX2 after having been grafted in the damaged brain of the recipient and can guide the recovery process has been studied.

LincRNA-COX2 has been studied in experiments in vitro on primary glia activated with MPTP.

The expression of lnc-RNA-COX2 has been studied by RT-PCR and it has been induced by the MPTP treatment of primary glia cultures (3 hours at 37°).

FISH analyses confirmed that lncRNA-COX2 is expressed in positive GFAP cells (that is glial cells) and its cell localization is related to the HuR cell distribution (RNA immunoprecipitation).

The RNA binding protein HuR/ELAVL1 binds to AU-rich elements (AREs) promoting the stabilization and translation of a given number of mRNAs into the cytoplasm, dictating their fate (D'Agostino et al., 2013).

The performed experiments show that the interaction with HuR seems necessary also for the activation of microglia, as denoted by IBA1 staining.

IBA1 is a protein specifically expressed in macrophages/microglia and is upregulated in microglia following nerve injury, central nervous system ischemia, and several other brain diseases. Incubation of glial cell primary cultures with MPTP or LPS for 3 hours considerably enhances staining with specific anti-IBA1 antibodies (FIGS. 19A-B).

The treatment with diidrotansione (DI), an inhibitor of HuR binding RNAs that leads to its cytoplasm mislocalization causes the lnRNA-COX2 down-regulation in cells treated with MPTP or LPS (FIGS. 19A-B). Such reduction corresponds to the contraction of IL-6 mRNA increase (FIGS. 19A-B).

Also BAY11-7083 treatment, a specific lnRNA-COX2 inhibitor by blocking NFkB, opposes the increase of levels of IL6 mRNA.

Moreover in the same experimental conditions, microglial cells were incubated with the supernatant of hADSCs cultures.

FIG. 20 shows that the supernatant conditioned with hADSCs, derived from the mechanically activated fat, is able to particularly oppose the expression of lnRNA COX2 and IL-6 in MPTP or LPS activated primary glial cells.

The expression of lnRNA CCND1, a long non coding RNA referred to the promoter of cyclin D1, used as negative control, was not modified in any of the experimented conditions.

The recovery of motor functions of hind limbs after spinal injury was observed in mice after the transplantation of mechanically activated adipose tissue (MALS), while the lipoaspirate is inefficacious (FIGS. 21 and 22).

The spinal injury, induced by a contusion made by an impactor with a diameter of 1 mm that hits the exposed thoracic spinal cord at level T9 with a force of 70 Kdyne for 1 second, causes paralysis of the hind limbs that partially improves, less than 3 points according to BMS (Basso Mouse Scale) (FIG. 22). The transplantation of lipoaspirated fat (LS) does not cause considerable improvement, while the treatment with MALS causes a great improvement exceeding 6 points according to BMS. 9 points means a normal ambulation.

The mechanically activated adipose tissue (MALS) of the present invention was applied on the surface of the injured spinal cord, where it gradually penetrates while filling the injury area and by joining the two portions of the injured spinal cord and allowing for the nerve regeneration.

The anti-inflammatory action of the mechanically activated adipose tissue (MALS) is rapid and it suppresses the production of inflammatory cytokines in the injured spinal cord. After 48 hours from the injury, the factors released from the injured spinal cord knock down the production of I1-1 alpha, IL-1 beta and IL-6 in the injury site and in caudal and rostral portions of the injured spinal cord.

From what described above and with reference to the figures, it is clear how the application of a orbital shaking force with an intensity and for the time described and claimed in the present invention allows anti-inflammatory properties and stem properties of mesenchymal stem cells present in the adipose tissue lipoaspirated or removed with any other procedure from the human body to be activated with a minimal manipulation of cells.

The adipose tissue and/or stem cells of the present invention can be therefore used for therapeutic purposes, or also cosmetic purposes, for preparing medicines to be used during cell therapies.

The tissue and/or mesenchymal stem cells obtained by the method of the present invention can be:

used as a medicine, used for treating motor and coordination dysfunctions, used for treating Parkinson's disease, used for treating spinal cord injuries.

In particular the transplantation of tissue and/or mesenchymal stem cells derived from human adipose tissue hADSCs, mechanically activated as described and claimed herein, can promote the rapid recovery of motor functionalities in patients that have lost or reduced such mobility, such as for example patients suffering from Parkinson's disease. Moreover the activated adipose tissue is very efficacious in promoting functional recovery after spinal cord injury due to its anti-inflammatory properties and to its ability to penetrate in the injury and to promote nerve regeneration.

Experimental Procedures

Cell Culture

Two ml of mechanically activated adipose tissue were inoculated in 25 cm$^2$ flasks completely filled with culture medium known as "Dulbecco's modified Eagle's Medium" (DMEM, Invitrogen, Carlsbad, CA) supplemented with 20% fetal bovine serum (FBS, JRH Bioscience, Lenexa, KS, Lot 6G2146) and incubated at 37° C. in 5% CO2. Flasks were turned upside-down such that cells floated up and adhered to the top inner ceiling surface of the flask. After 15 days, the medium and tissue were removed and the flasks were turned upside-down so that the cells were oriented on the bottom. The medium was replaced every 4 days until the cells reached confluence (90-95% after about 30 days).

Histological Control Analyses and Lipoaspirate Mechanically Treated Tissues

Histological analyses were performed on fresh adipose tissue (with or without mechanical treatment) on samples from the same subject. Briefly, formalin-fixed paraffin-embedded tissue samples were processed for conventional histopathological examination and immunohistochemistry.

Standard 4 micron thick tissue sections stained with hematoxylin and eosin (H&E) were examined by direct wide field light microscopy. For immunohistochemistry, four paraffin samples were sectioned (4 μm thickness), de-paraffined, and re-hydrated in xylene and graded concentrations of ethanol to distilled water. Then they were rinsed with PBS, treated with blocking solution (PBS+1% V/V fetal bovine serum for 1 hour at room temperature) and incubated with primary antibodies overnight at 4° C. After treatment with primary antibodies, the sections were washed with PBS and incubated with appropriate secondary antibodies. Endogenous peroxidase activity was quenched with 3% hydrogen peroxide in distilled water for 10 min. Staining was performed with 3,3' diaminobenzidine (DAB) as a chromogen (DAKO EnVision detection kit). In control determinations, primary antibodies were omitted and replaced with equivalent concentrations of unrelated IgG of the same subclass. The following primary antibodies were used: Vimentin (1:5000; Dako Cytomatic); 5100 (1:2000; Novocastra); β-Tubulin III (1:6000; Covance); human Nestin (1:2000; Millipore); Nanog (1:1000; Novus).

For immunofluorescence studies, cells were washed with PBS, fixed with paraformaldehyde (4% in PBS) treated with blocking solution and incubated with primary antibody anti β-Tubulin III (1:6000; Covance) overnight at 4° C.

After treatment with primary antibody, sections were washed with PBS and incubated with secondary antibody (Alexa Fluor® 555 goat anti-mouse 1:200 Molecular Probes®, Invitrogen, Life Technologies Italia, Monza, Italy) for 2 hours at room temperature. Nuclei were stained with DAPI (Hoechst 1/1000) and then mounted using the FluorSave Reagent (Calbiochem, Merck Chemical, Darmstadt, Germany) and analyzed by immunofluorescence microscopy (Leica 5500). As negative reference for the confocal analysis we used a consecutive section that was stained by omitting primary antibody anti β-Tubulin III and replacing it with equivalent concentrations of unrelated IgG of the same subclass.

Extraction of RNA and qRT-PCR Analysis

Cell RNAs were extracted using TRI Reagent® (Sigma-Aldrich, St. Luis, MO, USA) according to manufacturer's instructions. RNA purity and quantity was assessed by Nanodrop (Fisher Scientific) (A260/A280 1.8-2 was considered suitable for further analysis), possible contaminating DNA was removed and cDNA was prepared from 1 mg of RNA using "high Capacity RNA-to-cDNA" Kit (Applied Biosystems, Foster City, CA, USA).

Gene Expression of Adipose Tissues

Quantitative results were obtained by the real-time SYBR-Green assay (Euroclone spa Milano, ITALIA) on total RNA extracted using TRI Reagent® (Sigma-Aldrich, St-Luis, MO, USA) treated with DNasi I-Rnasi free (Ambion inc. Foster City, CA, USA) and reverse-transcripted using the "high Capacity cDNA Reverse kit Transcription" kit (Ambion Inc. Foster City, CA, USA) as suggested by the manufacturer. Differentially expressed genes were recognized by applying a significance threshold on t test at unequal variance.

ChIP on Adipose Tissue

Chromatin Immunoprecipitation was performed on 1 ml of mechanically treated or not treated lipoaspirated adipose tissue, as described in Haim et al., 2013.

G-Banding Karyotype Analysis

Cytogenetic analyses were performed on "in situ" cultures obtained by inoculating hADSCs directly into a coverslip inside Petri dishes containing 2 ml of medium (aMEM). Cells were treated with Colcemid (0.02 ml/ml) (Life Technologies a Carlsbad, CA, United States of America) for 90 minutes, hypotonic solution (1:1 Na citrate 1%: NaCl 0.3%) (Sigma-Aldrich, St. Louis, MO, USA) and fixative solution of 3:1 methanol:acetic acid (VWR International Radnor, Pennsylvania, USA), replaced twice. At least twenty-five QFQ banding metaphases were observed for each sample. The image was acquired using a fluorescence microscope (BX 60 Olympus) and analyzed with Powergene PSI system.

Formation of Spheroids hADSCs derived from mechanically activated lipoaspirated tissue were cultured in alpha-MEM medium with fetal bovine serum (20%) to reach 85% confluence at passage 1. Alpha-MEM medium was removed cells were washed twice with sterile PBS, therefore medium for neurospheres was added containing bFGF (20 ng/ml) and FEG (10 ng/ml) with no serum (Gritti et al., 2002).

Cell Culture THP-1 Culture Cells and Activation With LPS

THP-1 cells (202-TIB; ATTC, Rockville, Md.) were grown in suspension in RPMI 1640 media supplemented with 10% fetal calf serum (FCS), 50 U/mL penicillin, and 50 µg/mL streptomycin in 150 cm² flasks. Cell cultures and all experiments were carried out at 37° C. in 5% CO2 and 95% room air. Cells were passaged every 3 days and used between passages 3 and 12. Anti-inflammatory action of hADSCs cells was analysed in Trans-Well® culture system on 6 plates.

hADSCs were plated in well below at density of 1.5/104 cells/well in alpha-MEM medium. Twenty-four hours after their adhesion THP-1 cells were added in the well above at density of 75×104 cells/well. To induce release of IL-1 beta, lipopolysaccharide (LPS) was administered at the final concentration of 10 micrograms/ml. After three hours of incubation, supernatants were harvested in ice and immediately frozen. Release of IL-1 beta was studied by immunoblotting.

Experimental Animal Model for Parkinson's Disease and Cell Injection

MPTP (1-methyl-4-phenyl-1,2,3,6-tetrahydropyridine) is a neurotoxin precursor to MPP+, which causes permanent symptoms of Parkinson's disease by destroying dopaminergic neurons in the substantia nigra of the brain. It has been used to study disease models in various animal studies.

Injection of MPTP causes rapid onset of Parkinsonism, hence users of MPPP contaminated with MPTP will develop these symptoms. After two months, CSBL/6J mice were subjected of a first intraperitoneal injection of MPTP (36 mg/kg). Motor dysfunctions were evaluated every 2 days for the following 7 days, then animals were subjected to a second injection (20 mg/kg). After 3 days (day 10) cells were injected by stereotaxic surgery into the striatum. Coordinates, in relation to bregma, were: 0.1 mm posterior, 2.4 mm mediolateral, and 3.6 mm dorsal. Control group was injected only with 5 ml of sterile PBS or with hADSCs obtained from mechanically activated adipose tissue.

Labeling of PKH26 Cells

"PKH26 Cell Linker" Kits provide fluorescent labeling of live cells over an extended period of time, with no apparent toxic effects. "Fluorescent Linker" Kits are effective for a variety of cell types and exhibit no significant leaking, or transfer from cell to cell. They provide stable, clear, intense, accurate and reproducible fluorescent labeling of cells. For transplantation experiments 1×105 cells were injected in each animal.

Before each transplantation hADSCs were labelled with PKH26 and staining was performed according to the manufacturer protocol (Sigma-Aldrich C)). For the injection PKH26 positive cells were dissolved in sterile PBS at a concentration of 1×105 cells/5µl.

Evaluation of Motor Dysfunctions

Changes in the level of motor dysfunction can be used as a non invasive manner for evaluating alterations in the number of DArgic neurons and/or in the amount of DA in PD animal models, as mice systemically administered with 1-methyl-4-phenyl-1,2,3,6-tetrahydropyridine (MPTP). In this study DA-associated motor dysfunctions were evaluated by the "vertical grid test" and "horizontal grid test".

In the "horizontal grid test" device once the mouse firmly grabbed on the grids with all four paws, the apparatus was turned upside down and the animal was videotaped for a maximum duration of 30 seconds.

With each step, the paw may fall or slip between the wire of the grid. This was recorded as a "foot fault". The total number of steps (movement of each forelimb) that the mouse used to cross the grid was counted, and the total number of foot faults for each forelimb were recorded.

The Vertical grid test was performed by placing the mouse 3 cm from the top of a vertical grid, facing upward, and was videotaped while it turned around and climbed down the grid. The time required to climb down starting from said top edge was measured.

The recovery of motor functions of hind limbs after spinal cord injury, induced by a contusion made by an impactor with a diameter of 1 mm that hits the exposed thoracic spinal cord at level T9 with a force of 70 Kdyne for 1 second, was evaluated by observing the use of hind limbs in the "free locomotion" test. The used scale (BMS, Basso Mouse Scale) describes the several recovery levels of motility from 0 that means a paralysis of hind limbs to 9 that means a normal locomotion. The value reached by the treatment with saline and lipoaspirate was about 3 points (plantar positioning of the paw with poor ability in supporting the body) while MALS led to overcome 6 points in the scale corresponding to a frequent or consistent plantar positioning and mainly coordinated positioning of the paws with support of the body.

FIGS. 24 to 27 show a further embodiment of the application of the invention wherein activated adipose cells that is MALS allow endogenous stem cells of the spinal cord to be activated for the treatment of the spinal cord. As it is clear in presence of an injury, as a contusion of the spinal cord at 70 Kdyne. FIG. 24d shows the contusion treated with MALS. FIGS. 25a to 25d show enlarged details of ependymal stem cells activated by activated adipose cells that is the application of MALS.

After 4 weeks from the activation by MALS the treatment provided the results visible in FIGS. 26 and 27. It is noted the formation of new neurons in the grey matter of the injured spinal cord due to the migration of ependymal stem cells activated by MALS.

The invention claimed is:

1. A method for promoting anti-inflammatory properties and for improving repair ability of a tissue containing mesenchymal stem cells (MSCs), comprising:

mechanically activating an adipose tissue by applying an orbital shaking force on the adipose tissue that has been lipoaspirated or removed from a body, wherein the orbital shaking force has an intensity ranging from 40 to 120×g and is applied for a time ranging from 3 to 20 minutes, thereby obtaining an activated adipose tissue having improved anti-inflammatory properties and improved repair ability.

2. The method according to claim 1, wherein the applied orbital shaking force has an intensity equal to 97×g.

3. The method according to claim 1, wherein said orbital shaking force is applied for 10 minutes.

4. The method according to claim 1, wherein mechanically activating comprises applying the orbital shaking force that is repeated two or more times with an equal or different force intensity each time, or with an equal or different force application duration for each time.

5. The method according to claim 1, wherein said lipoaspirated adipose tissue is cryopreserved.

6. The method according to claim 1, further comprising a step of isolating and expanding the mesenchymal stem cells contained in said adipose tissue that has been lipoaspirated or removed from the body.

7. The method according to claim 6, wherein the step of isolating and expanding the mesenchymal stem cells contained in said adipose tissue that has been lipoaspirated or removed from the body comprises:

inoculating 2 ml of the activated adipose tissue in a 25 $cm^2$ flask completely filled with culture medium "Dulbecco's modified Eagle's Medium" (DMEM) supplemented with 20% fetal bovine serum;

incubating at 37° C. in 5% $CO^2$;

turning upside-down the flask such that cells float up and adhere to a top inner ceiling surface of the flask;

removing the culture medium and tissue after 15 days and turning upside-down the flask so that the cells are on a bottom of the flask; and replacing the culture medium every 4 days until reaching cell confluence of 90-95%.

\* \* \* \* \*